US007176286B2

(12) United States Patent
Gargano et al.

(10) Patent No.: US 7,176,286 B2
(45) Date of Patent: Feb. 13, 2007

(54) ANTIGEN FRAGMENTS FOR THE DIAGNOSIS OF *TOXOPLASMA GONDII*

(75) Inventors: Nicola Gargano, Pomezia (IT); Elisa Beghetto, Pomezia (IT); Manlio Di Cristina, Pomezia (IT); Franco Felici, Pomezia (IT)

(73) Assignee: Kenton S.R.L., Pomezia (Rome) (IT)

( * ) Notice: Subject to any disclaimer, the term of this patent is extended or adjusted under 35 U.S.C. 154(b) by 0 days.

(21) Appl. No.: 10/508,622

(22) PCT Filed: Mar. 18, 2003

(86) PCT No.: PCT/IT03/00162

§ 371 (c)(1),
(2), (4) Date: Dec. 10, 2004

(87) PCT Pub. No.: WO03/080839

PCT Pub. Date: Oct. 2, 2003

(65) Prior Publication Data
US 2005/0089867 A1  Apr. 28, 2005

(30) Foreign Application Priority Data
Mar. 21, 2002 (IT) .................. RM2002A0159
Nov. 13, 2002 (IT) .................. RM2002A0568

(51) Int. Cl.
C07K 1/00 (2006.01)
A61K 38/00 (2006.01)
A61K 39/012 (2006.01)
C12N 15/09 (2006.01)
C12N 7/00 (2006.01)

(52) U.S. Cl. .................. 530/350; 530/300; 530/387.1; 435/273.1; 435/69.3; 435/235.1; 435/320.1; 424/184.1

(58) Field of Classification Search .......... 435/320.1, 435/235.1, 69.1, 471, 69.3; 424/273.1, 184.1, 424/278.1; 530/350, 300, 387.1, 388.6
See application file for complete search history.

(56) References Cited

U.S. PATENT DOCUMENTS 6,022,546 A * 2/2000 Knapp et al. ............ 424/273.1
6,392,014 B1 * 5/2002 Cesbron et al. ............ 530/350
6,420,540 B1 * 7/2002 Koolen et al. ............ 536/23.1
2002/0172985 A1 * 11/2002 Jacobs et al. ............ 435/7.22
2005/0210535 A1 * 9/2005 Ward et al. .................. 800/8

OTHER PUBLICATIONS

Cesbron-Delauw et al (Molecular characterization of a 23-kilodalton major antigen secreted by *Toxoplasma gondii*, Proc. Natl. Acad. Sci. USA, 1989; 86(19): 7537-7541).*
Beghetto et al (Identification of a human immunodominant B-cell epitope within the GRA1 antigen of *Toxoplasma gondii* by phage display of cDNA libraries, International Journal for Parasitology, 2001; 31: 1659-1668).*
Coughlan et al (Cellular and humoral immune response to recombinant antigens in sheep infected with *Toxoplasma gondii*, Parasite Immunology, 1995; 17: 465-468).*
Velge-Roussel et al (Epitopic analysis of the *Toxoplasma gondii* major surface antigen SAG1, Molecular and Biochemical Parasitology, 1994; 66: 31-38).*
Beghetto et al; "Molecular Dissection of the Human B-Cell Response Against *Toxoplasma gondii* Infection by Lambda Display of cDNA libraries"; International Journal for Parasitology, vol. 33, No. 2, Feb. 20, 2003, pp. 163-173, XP001153939.
Beghetto et al; "Identification of a Human Immunodominant B-Cell Epitope Within the Grai Antigen of *Toxoplasma gondii* by Phage Display of cDNA Libraries"; International Journal for Parasitology, vol. 31, 2001, pp. 1659-1668, XP001063313.

* cited by examiner

*Primary Examiner*—Robert A. Zeman
*Assistant Examiner*—Lakia J. Tongue
(74) *Attorney, Agent, or Firm*—Nixon & Vanderhye P.C.

(57) ABSTRACT

The invention described herein relates to a method for identifying antigen fragments of *Toxoplasma gondii* proteins, and their use as diagnostic and immunogenic agents. Said method is implemented by means of selection of DNA fragments libraries of the parasite with sera of subjects who have been infected, using the phage display technique, and is characterised in that it uses the expression/exposure vector λKM4. The method allows also to identify antigen fragments related to the time of the infection.

4 Claims, 1 Drawing Sheet

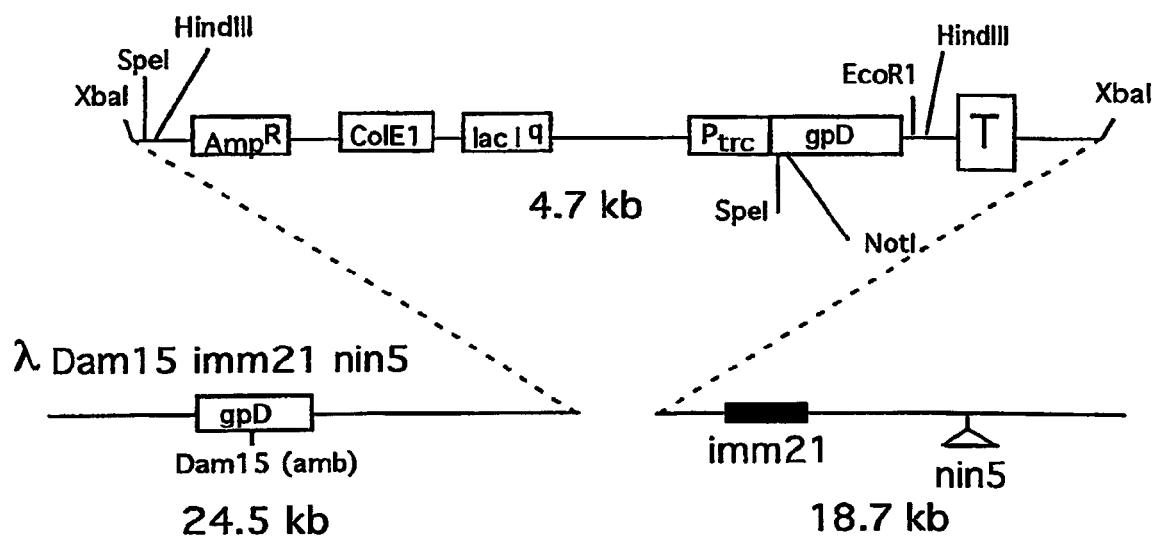
Figura 1

ANTIGEN FRAGMENTS FOR THE DIAGNOSIS OF *TOXOPLASMA GONDII*

This application is the US national phase of international application PCT/IT03/00162 filed 18 Mar. 2003, which designated the US and claims benefit of IT Application No. RM02A000159 filed 21 Mar. 2002 and IT Application No. RM02A000568 filed 13 Nov. 2002, the entire contents of each of which are incorporated herein by reference.

The invention described herein relates to a method for identifying antigen fragments of *Toxoplasma gondii* proteins, and their use as diagnostic and immunogenic agents. Said method is implemented by means of selection of cDNA libraries of the parasite or of DNA fragments of specific genes of the parasite with sera of subjects who have been infected by the parasite, using the phage display technique, and is characterised in that it uses the vector λKM4.

The invention described herein also relates to the technical field of the preparation of diagnostic means not applied directly to the animal or human body and furnishes compounds, methods for their preparation, methods for their use and compositions containing them which are suitable for industrial application in the pharmaceutical and diagnostic field, particularly for the detection and diagnosis of *Toxoplasma gondii* infections, as well as for the treatment and prevention of said infections.

BACKGROUND TO THE INVENTION

Early diagnosis is a priority and highly desirable objective in all fields of medicament, particularly because it allows an appreciable improvement in the patient's life and a concomitant saving on the part of health care systems or on the part of the actual patients. In the particular case of the invention described herein, early diagnosis is that of potential or existing *Toxoplasma gondii* infection in pregnant women, with particular concern for the health of the foetus, and in infected subjects, particularly those with impaired immunity.

*Toxoplasma gondii* is an obligate intracellular parasite that infects all mammalian cells, including those of human subjects (McCabe and Remington, *N. Engl. J. Med.* 1988, 318–313–5), and other animal genera, e.g. birds. The life cycle of the parasite is complex and one may distinguish between three stages of infection: tachyzoite (asexual), bradyzoite (in tissue cysts, asexual) and sporozoite (in oocysts, sexual reproduction). Transmission typically occurs through ingestion of undercooked meat harbouring tissue cysts or vegetables contaminated with oocysts shed by cats. Human infection is generally asymptomatic and self-limiting in immunocompetent hosts. In contrast, in subjects with impaired immunity (particularly those affected by AIDS), toxoplasmosis is a severe opportunist infection, which may give rise to encephalitis with very serious outcomes (Luft, B. J., Remington J. S., 1992, *Clin. Infect. Dis.* 15, 211–22). Moreover, contracting primary infection during pregnancy may lead to miscarriages or to severe foetal disease in mammals.

For an extensive overview of the problem of toxoplasmosis the reader is referred to the specialistic medical literature.

Diagnosis of *T. gondii* infection is established by isolating the micro-organism in the blood or body fluids, identifying the parasite in tissues, detecting specific nucleotide sequences with PCR, or by detecting specific anti-*T. gondii* immunoglobulins produced by the host in response to the infection (Beaman et al., 1995 *Principles and Practice of Infectious Diseases* 4th Ed., Churchill Livingstone Inc., New York, 2455–75; Remington J S et al. 1995, *Infectious Diseases of the Fetus and Newborn Infant*, W. B. Saunders, Philadelphia, Pa., 140–267).

One of the main problems in diagnosing *T. gondii* infections has to do with pregnant women. To implement suitable therapies in good time and avoid possible damage to the foetus it is very important to establish if parasitic infection occurred before or after conception. This is generally done by attempting to detect the presence of the various classes of anti-Toxoplasma immunoglobulins (IgG, IgM, IgA, avidity of IgG). For this reason, the availability of specific, sensitive diagnostic agents is desirable.

*T. gondii* antigens have long been known and available, first of all as antigen mixtures obtained in various ways (FR 2,226,468, Mérieux; SU 533376, Veterinary Research Institute; JP 54044016, Nihon Toketsu Kanso), then as subsequent isolations of pure antigens (EP 0 082 745, Mérieux; EP 0 301 961, INSERM, Pasteur; WO 89/5658, Transgene) and their characterisation both as proteins, and of their respective genes (WO 89/08700, U. Leland, Dartmouth Coll.; U.S. Pat. No. 4,877,726, Res. Inst. Palo Alto; WO 89/12683, INSERM, Pasteur; EP 0 391 319, Mochida Pharm.; IT 1,196,817, CNR; EP 0 431 541, Behringwerke; WO 92/01067, CNRS; WO 92/02624, U. Flinders; WO 92/11366, Innogenetics, Smithkline Beecham; U.S. Pat. No. 5,215,917, Res. Inst. Palo Alto; WO 92/25689, FR 2702491, INSERM, Pasteur; WO 96/02654, bioMeriéux, Transgene; EP 0 710 724 Akzo; EP 0 724 016, bioMeriéux; EP 0 751 147, Behringwerke; U.S. Pat. No. 5,633,139, Res. Inst. Palo Alto; WO 97/27300, Innogenetics; U.S. Pat. No. 5,665,542, U.S. Pat. No. 5,686,575, Res. Inst. Palo Alto; WO 99/32633, Heska; JP 11225783, Yano; WO 99/61906, Abbott; WO 99/66043, Smithkline Beecham; JP 2000300278, Yano; WO 00/164,243, Virsol).

Numerous studies have found various different antigenic proteins of *T. gondii* and the gene sequences of these have also been determined.

Among the most interesting proteins both for diagnostic and therapeutic purposes, in the form of vaccines, we should mention: the surface antigens SAG1 (or P30) (WO 89/08700, Stanford University; WO 89/12683 Pasteur, INSERM; WO 94/17813, WO 96/02654, Transgene, bioMeriéux; EP 0 724 016, WO 99/61906, U.S. Pat. No. 5,962,654, Harning et al., *Clinical and Diagnostic Laboratory Immunology*, May 1996, 355–357); SAG2 (or P22) (Parmley et al., 1992, *J. Clin. Microbiol.* 30, 1127–33); the dense granule proteins GRA1 (or P24) (EP 0 301 961, Pasteur, INSERM; WO 89/05658, Transgene, Cesbron-Delauw, et al., 1989 *P.N.A.S. USA* 86, 7537–41); GRA2 (or P28) (WO 93/25689, INSERM, Pasteur; U.S. Pat. No. 5,633,139, U.S. Pat. No. 5,665,542, U.S. Pat. No. 5,686,575, Res. Inst. Palo Alto; Prince et al., *Mol. Biochem. Parasitol.*, 34 3–14); GRA4 (Mevelec et al., *Mol. Biochem. Parasitol.* 56, 227–38); GRA6 (or P32) (FR 2,702,491, INSERM, Pasteur; Lecordier al., *Mol. Biochem. Parasitol.* 70, 85–94); GRA7 (WO 99/61906, Abbott; Jacobs et al., *Mol. Biochem. Parasitol.* 91, 237–49); GRA3 (Robben et al. 2002, J. Biol. Chem. 277, 17544–47): the rhoptry antigens ROP1 (or P66) (U.S. Pat. No. 5,976,553, U. Leland; EP 0 431 541, Innogenetics); ROP2 (or P54) (Sharma et al., *J. Immunol.*, 131, 377–83).

As described in the above-mentioned references, the antigens were obtained with well-known recombinant cDNA techniques in expression vectors. For example, for the antigen SAG1, WO 98/08700 uses known expression vectors in phage λgt11. WO 98/12683 uses the same phage and transfects *E. coli* with a proprietary plasmid, or by preparing a special expression cassette, as in WO 96/02654. EP 0 724 016 obtains mimotypes, using combinatorial expression libraries of peptides. EP 0 301 961 describes how to obtain excretion-secretion antigens with molecular weights ranging from 20 kDa to 185 kDa. WO 89/05658 describes a protein containing the epitopes of the 24 kDa protein recognised by the antibodies produced against *Toxoplasma* excretion-secretion antigens; this protein is obtained by transfection of cells by means of expression vectors. The antigen P28 (GRA2) is described in U.S. Pat. No. 5,633,139 and the method of obtaining it is again implemented through expression in phage λgt11. The antigen P32 (GRA6) is described in patent FR 2,702,491, the antigen ROP1 (P66) in U.S. Pat. No. 5,976,553, P35 (or GRA8) in EP 0 431 541, WO 99/57295 and WO 99/61906, and lastly P68 in EP 0 431 541.

It should be stressed that all these antigens are obtained by means of molecular biology techniques that use the expression of proteins in bacterial cells. None of the documents cited describe the technique of expression/exposure of libraries of cDNA deriving from *Toxoplasma gondii* in the lambda phage (phage display) to obtain fragments of antigens of the pathogen.

The invention described herein uses a new vector of DNA expression and protein exposure as molecular fusion with the amino-terminal part of protein D of the lambda bacteriophage capsid (pD) (λKM4).

The expression/exposure vector was described for the first time in patent application PCT/IT01/00405, filed on 26 Jul. 2001, the most important part of which is incorporated herein. This vector, called λKM4, differs from that used in expression only experiments (λgt11) in that the recombinant protein coded for by the DNA fragment is expressed as fusion with a protein of the bacteriophage itself and then exposed on the capsid. According to the vector project, the phage exposes the protein fragment on the surface only if its open reading frame (ORF) coincides with pD. The size of the fragments of DNA cloned in our libraries was selected in order to represent a population of medium size ranging from 300 to 1000 nucleotide base pairs (bp), and, for statistical reasons, most of the out-of-frame sequences contain stop codons which do not permit their translation and consequently exposure on the surface of the phage.

SUMMARY OF THE INVENTION

It has now been found that the combination of the affinity selection and phage display techniques, together with the use of the vector KM4, provides a method for the identification of specific antigen fragments of *Toxoplasma gondii* by means of the selection of display libraries of DNA fragments with sera of infected individuals. DNA fragments are obtained either from cDNA of whole parasite or from DNA encoding for known specific gene products. With this method it proves possible to identify antigen fragments from very large libraries (i.e. expressing a large number of different sequences). The antigen fragments thus identified enable specific ligands to be obtained, which in turn can be used as diagnostic and therapeutic means.

Therefore, one object of the invention described herein is a method for the identification of antigen fragments of *Toxoplasma gondii* proteins, by means of the selection of libraries of DNA fragments with sera of subjects who have been infected by the parasite, using the phage display technique, characterised in that it uses the vector λKM4.

Another object of the present invention are antigen fragments obtainable with the above-mentioned method, both isolated and characterised, and as sets of antigen fragments called "collections". The invention described herein also extends to the antigen portions of said fragments (epitopes).

The use of said antigen fragments as diagnostic agents and the related diagnostic aids containing them, for example in the form of kits or other supports, constitute a further object of the present invention.

The use of said antigen fragments as active agents, particularly with an immunogenic action, for the preparation of medicaments for the prevention and therapy of *Toxoplasma gondii* infection, constitute a further object of the present invention.

Another object of the present invention are the gene sequences coding for the above-mentioned antigen fragments, their use as medicaments, particularly for the prevention and therapy of *Toxoplasma gondii* infection, e.g. as gene therapy. The present invention also extends to the gene sequences that hybridise with the sequences of the above-mentioned fragments in stringent hybridisation conditions.

Another object of the present invention are anti-epitope antibodies and their use in the preparation of diagnostic, preventive and therapeutic means, e.g. as conjugates with active ingredients such as chemo-therapy agents. Antibodies can be generated also against collections of said epitopes.

The method provided by the present invention makes it possible to confirm the use of the *Toxoplasma gondii* antigens described above as such as diagnostic agents and also to identify in known antigens the epitopes that trigger an immune response in human subjects; this portion is a further object of the present invention; but it also makes it possible to identify the antigenic function of proteins of *Toxoplasma gondii*, or of portions thereof, which, though their structure and possibly their physiological function may be known, are unknown as regards their antigenic function, and such function comes within the framework of the present invention; lastly, the method according to the present invention also provides new antigen fragments of *Toxoplasma gondii* proteins, that constitute yet another object of the present invention.

Another object of the present invention is the use of the antigen fragments thus identified for the preparation of means of diagnosing the infection, as well as the actual diagnostic means containing them. The use realtes also to the diagnosis of the time of the infection, in particular by the IgG avidity assay.

Another object of the present invention is the use of the antigen fragments thus identified as medicaments, particularly for the preparation of formulations, and particularly in the form of vaccines, which are useful for the prevention and cure of the infection. The vaccines according to the present invention are suitable for use in humans and other animals (particularly pigs, cats, sheeps).

Another object of the present invention are ligands generated from the above-mentioned antigen fragments and the related collections and the use of such ligands for the preparation of diagnostic means for the detection of the infection, with particular reference to the time of infection, as well as therapeutic means for the prevention and treatment of the infection itself.

Another object of the present invention is a method for the diagnosis of *Toxoplasma gondii* infection, comprising the selection of sera of subjects affected or suspected of being affected by said infection with the above mentioned antigen fragments and/or their collection and/or at least one ligand and/or antibody.

These and other objects will be illustrated here below in detail, also by means of examples and figures, where FIG. 1 represents the map of the vector λKM4.

DETAILED DESCRIPTION OF THE INVENTION

The present invention comprises the construction of expression/exposure libraries of DNA fragments prepared from *Toxoplasma gondii* cells, the selection of such libraries with the sera of patients who have been infected by *Toxoplasma gondii*, the characterisation of the antigen fragments, and the use of said fragments for developing selective diagnostic means.

Optionally, the present invention may entail the generation of specific ligands for said antigen fragments (e.g. human recombinant antibodies or humanised murine recombinant antibodies) and the construction of selective diagnostic means that incorporate the ligands generated.

Antibodies and ligands of the present invention can be obtained according according to the general common knowledge and conventional methods.

The method according to the present invention advantageously combines affinity selection and the power of phage display.

What is meant by phage display, as understood by the person of ordinary skill in the art, is a strategy based on the selection of expression/exposure libraries in which small protein domains are exposed on the surface of bacteriophages containing the corresponding genetic information.

The method implemented according to the present invention for the first time provides new and advantageous analysis possibilities:

the use of small amounts of serum to identify antigen fragments of the infectious agent, the possibility of selecting only the domains responsible for the interaction with the antibodies, without having to express the entire gene, the product of which may be insoluble or toxic;

lastly, the possibility of effecting successive cycles of selection using sera from different patients or mixtures of sera facilitates the identification of cross-reactive antigens which represent one of the main objectives of the present invention.

For the above-mentioned reasons, for each library, messenger RNA was purified from an adequate number of cells (e.g. $10^6$ cells), using common commercially available means, from which the corresponding cDNA was generated. The latter was fragmented (by means of the bacterial enzyme DNaseI) and then cloned in the expression/exposure vector λKM4 (see example).

In the other embodiment, relating to specific *T. gondii* gene, each specific *T. gondii* gene, was amplified from the DNA of the parasite (either cDNA or genomic DNA, both prepared by using common commercially available kits) by means of PCR with specific synthetic oligonucleotides. DNA of single genes was then fragmented randomly by means of the bacterial enzyme DNaseI and then cloned as a pool in the expression/exposure vector λKM4.

The amplification of the libraries was done by means of normal techniques with which the expert in the field is familiar, e.g. by plating, growth, elution, purification and concentration (Sambrook et al., 1989, *Molecular Cloning: a laboratory manual*, Cold Spring Harbor Laboratory Press, NY). The libraries were then used to develop the selection conditions, screening and characterisation of the sequences identified. Lastly, the phage clones identified were characterised by immunoenzymatic assays.

A library of the phage display type, constructed using cDNA deriving from cells of pathogenic organisms, makes it possible to exploit affinity selection, which is based on incubation of specific sera (reactive with the pathogen) with collections of bacteriophages that express portions of proteins of the pathogen on their capside and that contain the corresponding genetic information. The bacteriophages that specifically bind the antibodies present in the serum are easily recovered, remaining bound (by the antibodies themselves) to a solid support (e.g. magnetic beads); the non-specific ones, by contrast, are washed away. Direct screening, i.e. the analysis of the ability of single phage clones to bind the antibodies of a given serum, is done only at a later stage, when the complexity of the library (i.e. the different number of sequences) is substantially reduced, precisely as a result of the selection.

The use of selection strategies allows faster analysis of a large number of different protein sequences for the purposes of identifying those that respond to a particular characteristic, e.g. interacting specifically with antibodies present in the serum of patients who have been infected by the pathogen. What is more, the combination of affinity selection and phage display makes it possible to use a smaller amount of serum for each analysis. The direct screening of a classic cDNA library, in fact, entails the use of large amounts of serum, which are not always easy to obtain. For example, to analyse a library of approximately $10^6$ independent clones it would be necessary to incubate along with the preselected serum the numerous filters containing a total of approximately $10^7$ phage plaques transferred from the different culture plates with the infected bacteria (e.g. a serum volume of 1–10 ml). The use of a display-type library, on the other hand, permits affinity selection in small volumes (0.1–1 ml) prior to direct screening, and from limited amounts of serum, such as, for example, 10 μl.

Lastly, given that a very large number of bacteriophages can be contained in small volumes (e.g. $10^{11}$ phage particles are normally contained in a volume of 0.1 ml), and affinity selection is done in small volumes (0.1–1 ml), a further advantage of the use of display-type libraries consists in analysing a number of independent clones (particles of recombinant phages exposing different cDNA sequences on their surfaces) 10–100 times greater (e.g. $10^8$ different bacteriohages) than expression-alone libraries where, as a result of technical problems, not more than $10^6$ independent clones are normally analysed.

As regards industrial applicability, one possible realisation of the present invention is in the form of diagnostic kits containing the antigen fragments and/or ligands and/or antibodies described above.

The diagnostic kits which are the object of the present invention are known to the expert in the field and do not require any particular description. By way of an example, the reader is referred to the patent literature cited above, to which may be added U.S. Pat. No. 6,265,176 and WO 01/63283 as further references.

Similar considerations hold good for the therapeutic application, where the preparation of medicaments or vaccines comes within the framework of general knowledge; for further reference purposes the reader is again referred to the patent literature cited in the present description.

The invention will now be illustrated in greater detail by means of examples and figures, where FIG. 1 presents the map of the vector λKM4.

EXAMPLE 1

Construction of the Vector λKM4

This technique is described in international patent application No. PCT/IT01/00405, filed on 26 Jul. 2001 and incorporated herein for reference purposes, explicitly mentioning the references cited therein. FIG. 1 represents the map of the vector λKM4. The plasmid pNS3785 (Sternberg and Hoess, 1995, *Proc. Natl. Acad. Sci. USA*, 92:1609–1613) was amplified by inverse PCR using the synthetic oligonucleotides 5'-TTTA<u>TCTAGA</u>CCCAGC<u>CCTAGG</u>AAGCTTCTCCTGAGTAGGACAAATCC-3' (SEQ ID No 1) bearing the sites XbaI and AvrII (underlined) for the subsequent cloning of the lambda phage, and 5'-GGG<u>TCTAGA</u>TAAAACGAAAGGCCCAGTCTTTC-3' (SEQ ID No 2) bearing the site XbaI. In inverse PCR a mixture of Taq DNA polymerase and Pfu DNA polymerase was used to increase the fidelity of the DNA synthesis. Twenty-five amplification cycles were performed (95° C.-30 sec, 55° C.-30 sec, 72° C.-20 min). The autoligation of the PCR product, previously digested with XbaI endonuclease gave rise to the plasmid PKM3. The lambda gene pD was amplified with PCR from the plasmid pNS3785 using the primers 5'-CCGCCTTCCATGGGTACTAGTTTTAAAT GCGGCCGCACGAGCAAAGAAACCTTTAC-3' (SEQ ID No 3) e 5'-AGCTTCCTAGGGCTGGGTCTAG-3' (SEQ ID No 4) containing the restriction sites NcoI, SpeI, NotI and EcoRI, respectively, (underlined). The PCR product was then purified, digested with NcoI and EcoRI endonuclease and recloned in sites NcoI and EcoRI of pKM3, resulting in the plasmid pKM4 bearing only the restriction sites SpeI and NotI at the 5' end of the protein gpD. The plasmid was then digested with XbaI endonuclease and cloned in the XbaI site of the lambda phage Dam15imm21nin5 (Sternberg and Hoess, 1995, *Proc. Natl. Acad. Sci. USA.*, 92:1609–1613).

Construction of cDNA Library from Tachyzoites of *Toxoplasma gondii*

Tachyzoites of the protozoon *Toxoplasma gondii* (RH strain) were grown in vitro in monkey kidney cells ("VERO" African green monkey cells) using DMEM culture medium containing 10% foetal bovine serum, 2 mM glutamine and 0.05 mg/ml gentamicin (Gibco BRL, Canada). The parasites were collected after complete lysis of the host cells and purified by filtration (filter porosity 3 μm) followed by centrifuging. 4 μg of mRNA were isolated from $10^7$ tachyzoites using the "QuickPrep Micro mRNA Purification Kit" (Amersham Pharmacia Biotech, Sweden) and following the manufacturer's instructions. The double-helix cDNA was synthesised from 200 ng of poly(A)+ RNA using the "SMART cDNA Library Construction Kit" (Clontech, CA, USA) and following the manufacturer's instructions. 10 μg of total cDNA were then fragmented randomly using 0.5 ng of the endonuclease DNaseI (Sigma-Aldrich, USA). The mixture of cDNA and DNaseI was incubated for 20 minutes at 15° C. and the cDNA fragments were purified with extraction in phenol/chloroform and subsequent purification by means of the "QIAquick PCR Purification Kit" (Qiagen, CA, USA), following the manufacturer's instructions. The 3 μg ends of the cDNA fragments were "flattened" by incubating the DNA with 9 units of the enzyme T4 DNA polymerase (New England Biolabs, MA, USA) for 60 minutes at 15° C. The fragments were then purified by means of extraction in phenol/chloroform and subsequent precipitation in ethanol. 500 ng of the resulting DNA were bound with a 20-fold molar excess of "synthetic adaptors" for the purposes of adding the restriction sites SpeI and NotI to the ends of the fragments. Six adaptors were used, obtained by hybridisation of the following pairs of oligonucleotides: K185 5'-CTAGTCGTGCTGGCCAGC-3' (SEQ ID No 5) and K186 5'-GCTGGCCAGCACGA-3' (SEQ ID No 6); K187 5'-CTAGTCGTGCTGGCCAGCT-3' (SEQ ID No 7) and K188 5'-AGCTGGCCAGCACGA-3' (SEQ ID No 8); K189 5'-CTAGTCGTGCTGGCCAGCTG-3' (SEQ ID No 9) and K190 5'-CAGCTGGCCAGCACGA-3' (SEQ ID No 10); K191 5'-TCTGGTGGCGGTAGC-3' (SEQ ID No 11) and K192 5'-GGCCGCTACCGCCAC-CAGA-3' (SEQ ID No 12); K193 5'-TTCTGGTGGCGG-TAGC-3'(SEQ ID No 13) and K194 5'-GGCCGCTACCGC-CACCAGAA-3' (SEQ ID No 14); K195 5'-TTTCTGGTGGCGGTAGC-3' (SEQ ID No 15) and K196 5'-GGCCGCTACCGCCACCAGAAA-3'(SEQ ID No 16). The excess of unligated adaptors was removed from the ligation mixture by electrophoresis on 2% agarose gel and the cDNA fragments with molecular weights ranging from 300 bp to 1000 bp were excised from the gel and purified by means of the "Qiaquick gel extraction kit" (Qiagen, Calif., USA) following the manufacturer's instructions. The vector λKM4 was digested with SpeI/NotI and for the construction of the library 6 ligation mixtures were performed, each containing 0.4 μg of vector and approximately 7 ng of insert. After overnight incubation at 4° C. the ligation mixtures were packaged in vitro with the "Ready-To-Go lambda packaging kit" (Amersham Pharmacia Biotech, Sweden) and plated for infection of BB4 cells (bacterial cells of *E. coli* strain BB4; Sambrook et al., 1989, *Molecular Cloning: a laboratory manual*, Cold Spring Harbor Laboratory Press, NY). After overnight incubation at 37° C. the phage was eluted from the plates with SM buffer (Sambrook et al., 1989, *Molecular Cloning: a laboratory manual*, Cold Spring Harbor Laboratory Press, NY), purified, concentrated and stored at −80° C. in SM buffer containing 7% dimethylsulphoxide. The complexity of the library calculated as the number of total independent clones with inserts was $10^7$ clones.

Affinity Selection

Two distinct methods were used for selecting the phage library with human sera. In the first method 100 μl of magnetic beads coated with Protein G (Dynabeads Protein-G, Dynal, Norway) were incubated with 10 μl of human serum for 30 minutes at room temperature. The beads were then incubated for 1 hour at 37° C. with blocking solution consisting of: 5% skimmed milk powder in PBS (Sambrook et al., 1989, *Molecular Cloning: a laboratory manual*, Cold Spring Harbor Laboratory Press, NY), 0.05% Tween 20, and $MgSO_4$ 10 mM. Approximately $10^{10}$ phage particles of the library were added to the beads and diluted in 1 ml of blocking solution for a further 4-hour incubation at room temperature with weak stirring. In the second method 40 μl of "M280-Tosyl activated" magnetic beads (Dynal, Norway) were coated with human anti-IgM antibodies (Sigma-Aldrich, USA) following the manufacturer's instructions. The beads were then washed with PBS/TritonX-100 1% and incubated with 10 μl of human serum in 300 μl of blocking solution for 2 hours at room temperature. After washing the beads three times with washing solution (PBS, 1% TritonX100, 10 mM $MgSO_4$), $10^{10}$ phage particles of the library were added to the beads and diluted in 200 μl of blocking solution for a further 3-hour incubation at room temperature with weak stirring.

With both selection methods, the beads were washed 10 times with 1 ml of washing solution (PBS, 1% TritonX100, 10 mM $MgSO_4$). The bound bacteriophages were amplified for infection of BB4 cells added directly to the beads (1.2 ml per selection) and subsequent 30-minute incubation at room temperature. 12 ml of NZY-Top Agar (Sambrook et al., 1989, *Molecular Cloning: a laboratory manual*, Cold Spring Harbor Laboratory Press, NY) were added to the mixture of beads and cells and immediately poured onto NZY plates (2 15-cm Petri capsules for selection). The plates were incubated for 12–16 hours at 37° C. The next day the phages were collected from the plates by means of the addition of 15 ml of SM buffer per plate and stirring for 4 hours at room temperature. The phages were purified by precipitation in PEG/NaCl (20% polyethylene glycol, NaCl 1M) and finally resuspended in 5 ml of SM and stored at +4° C.

Selection of the Library with Human Sera

To identify the specific antigens of *T. gondii* an affinity selection procedure was used consisting of two "panning" cycles with one or more positive sera (that is to say sera deriving from a patient who tested positive for the presence of antibodies directed against the parasite), followed by an immunological screening procedure carried out with the same sera or, alternatively, by analysis of single clones taken at random from the mixture of selected phages. Preferably, the library was selected with 10 positive sera (T1, T2, T3, T4, T5, T6, T7, T8, T9 and T10), generating, after a single selection cycle, the corresponding mixtures p1$^I$, p2$^I$, p3$^I$, p4$^I$, p5$^I$, p6$^I$, p7$^I$, p8$^I$, p9$^I$ and p10$^I$. Each mixture was then subjected to a second affinity selection cycle with the same serum, according to the first strategy mentioned above, giving rise to a second series of mixtures (called p1$^{II}$, p2$^{II}$, p3$^{II}$, p4$^{II}$, p5$^{II}$, p6$^{II}$, p7$^{II}$, p8$^{II}$, p9$^{II}$ and p10$^{II}$). The initial characterisation by means of an enzyme-linked immunosorbent assay (Phage-ELISA) showed that some of the mixtures were more reactive with the corresponding serum used for the selection, thus confirming the efficacy of the library and the affinity selection procedure. Various positive clones were identified by means of immunoplate screening per plaque of reactive mixtures.

Phage-ELISA

Multi-well plates (Immunoplate Maxisorb, Nunc, Denmark) were coated, incubating 100 µl/well of anti-lambda polyclonal antibodies overnight at 4° C. with a concentration of 0.7 µg/ml in NaHCO$_3$ 50 mM, pH 9.6. After eliminating the coating solution, the plates were incubated with 250 µl of blocking solution (5% skimmed milk powder in PBS, 0.05% Tween-20). The plates were then washed twice with washing buffer (PBS, 0.05% Tween-20). A mixture of 100 µl of blocking solution containing phage lysate (diluted 1:1) was added to each well and incubated for 60 minutes at 37° C. 1 µl of human serum was preincubated for 30 minutes at room temperature with 10$^9$ wild-type phage particles, 1 µl of rabbit serum, 1 µl of bacterial extract of BB4 cells, 1 µl of foetal bovine serum in 100 µl of blocking solution. The plates were washed 5 times after incubation with the phage lysate and then incubated with the serum solution for 60 minutes at 37° C. The plates were then washed 5 times and incubated in blocking solution containing human anti-immunoglobulin antibodies conjugated with the enzyme peroxidase (Sigma-Aldrich, USA) diluted 1:10000 and rabbit serum diluted 1:40. After 30 minutes' incubation the plates were washed 5 times and the peroxidase activity was measured with 100 µl of TMB liquid substrate (Sigma-Aldrich, USA). After 15 minutes' development, the reaction was stopped by adding 25 µl of H$_2$SO$_4$ 2M. Lastly, the plates were analysed using an automatic ELISA reader (Multiskan, Labsystem, Finland) and the results were expressed as OD=OD$_{450\ nm}$–OD$_{620\ nm}$. The ELISA data were assessed as mean values of two independent assays.

Immunoscreening

Phage plaques were transferred from the bacterial medium to nitrocellulose filters (Schleicher & Schuell, Germany) by means of incubation at room temperature for 60 minutes. The filters were blocked for 60 minutes at room temperature in blocking solution (5% skimmed milk powder in PBS, 0.05% Tween-20). 40 µl of human serum were preincubated with 40 µl of bacterial extract of BB4 cells, 10$^9$ wild-type lambda phage particles in 4 ml of blocking solution. After eliminating the blocking solution, the filters were incubated with the serum for 3 hours at room temperature under stirring. The filters were then washed 5 times with washing buffer (PBS, 0.05% Tween-20) and then incubated for 60 minutes at room temperature, alternatively with human anti-IgG antibodies conjugated with alkaline phosphatase (Sigma-Aldrich, USA), or with human anti-IgM antibodies conjugated with alkaline phosphatase (Sigma-Aldrich, USA), both diluted 1:7500 in blocking solution. After washing the filters 5 times, 5 ml of development solution (substrates BCIP and NBT, Sigma-Aldrich, USA) were added and the development was interrupted by washing the filters in water.

Preparation of the Lambda Phage from Lysogenic Cells

Phage clones that proved positive at immunoscreening (direct screening) were isolated from the respective phage plaques and then amplified for subsequent characterisation. The bacterial BB4 cells were grown under stirring at 37° C. up to an optical density OD$_{600}$=1.0 in LB culture medium (Sambrook et al., 1989, Molecular Cloning: a laboratory manual, Cold Spring Harbor Laboratory Press, N.Y.) containing 0.2% maltose and 10 mM MgSO$_4$, recuperated by centrifuging and resuspended in SM buffer at optical density OD$_{600}$=0.2. 100 µl of cells were infected with recombinant bacteriophages recovered from single plaques, incubated for 20 minutes at room temperature, plated on LB medium with ampicillin (100 µg/ml) and then incubated for 18–20 hours at 32° C. A single bacterial colony was then grown in 10 ml of LB/ampicillin overnight at 32° C. under stirring. 500 ml of LB/ampicillin and MgSO$_4$ 10 mM were added to 5 ml of the overnight culture and incubated at 32° C. up to an optical density OD$_{600}$=0.6 under vigorous stirring. The culture was then incubated for 15 minutes in a water bath at 45° C. and then at 37° C. for a further 3 hours. After this, the bacteriophages were purified of the bacterial culture according to standard procedures (Sam brook et al., 1989, Molecular Cloning: a laboratory manual, Cold Spring Harbor Laboratory Press, NY) and stored at +4° C.

Lastly, the phage clones were analysed by means of phage-ELISA with a substantial panel of positive and negative sera. Clones whose ELISA value exceeded the background value, as obtained from the sum of the mean of the measurements of the negative sera and three times the standard deviation, were judged to be positive.

The following table 1 gives, by way of examples, the reactivity of a number of the recombinant bacteriophages selected.

TABLE 1

| Name of clone | Reactivity of phage clone with positive sera (positive/total pos.) | Reactivity of phage clone with negative sera (negative/total neg.) |
| --- | --- | --- |
| Tx-4.11 | 13/21 | 0/10 |
| TxM-17.2 | 4/8 | 1/8 |
| Tx-15.11 | 11/21 | 0/10 |
| Tx-1.11 | 19/21 | 0/10 |
| Tx-8.0 | 6/21 | 0/10 |
| Tx-1.16 | 20/21 | 0/10 |
| Tx-9.18 | 9/21 | 0/8 |
| Tx-7.11 | 21/21 | 0/10 |

Characterisation of Positive Clones

The clones which showed multiple reactivity with the Toxoplasma gondii positive sera and which presented no reactivity to the negative sera were subsequently sequenced and compared with various databases of sequences currently available (Non-Redundant Genbank CDS, Non-Redundant Database of Genbank Est Division, Non-Redundant Genbank+EMBL+DDBJ+PDB Sequences).

The sequences obtained can be classified in four groups:
  sequences that code for known T. gondii antigen fragments;
  sequences that code for known proteins which, however, are not known to be involved in the human antibody response;
  sequences that code for unknown proteins (e.g. EST);
  new sequences, not yet figuring in the databases.

The following table 2 gives, by way of examples, the sequences of some of the clones selected:

TABLE 2

| Name of clone | Sequence | Identification | Classification |
|---|---|---|---|
| Tx-4.11 (SEQ ID No 17) | AGTGGAGGGACAGGGCAGGGATTA GGAATCGGAGAATCTGTAGATTTG GAGATGATGGGGAACACGTATCGT GTGGAGAGACCCACAGGCAACCCG GACTTGCTCAAGATCGCCATTAAA GCTTCAGATGGATCGTACAGCGAA GTCGGCAATGTTAACGTGGAGGAG GTGATTGATACTATGAAAAGCATG CAGAGGGACGAGGACATTTTCCTT CGTGCGTTGAACAAAGGCGAAACA GTAGAGGAAGCGATCGAAGACGTG GCTCAAGCAGAAGGGCTTAATTCG GAGCAAACCCTGCAACTGGAAGAT GCAGTGAGCGCGGTGGCGTCTGTT GTTCAAGACGAG | GRA 1 known T. gondii antigen | Dense granule protein |
| TxM-17.2 (SEQ ID No 18) | TACTCTTCACCACGAATAGTTGTT TTGATTAGATATTGCTTCTTCTCC ACATATCGCCTCACAATGTTCGCC GTAAAACATTGTTTGCTGGTTGTT GCCGTTGGCGCCCTGGTCAACGTC TCGGTGAGGGCTGCCGAGTTTTCC GGAGTTGTTAACCAGGGACCT | GRA2 known T. gondii antigen | Dense granule protein |
| Tx-15.11 (SEQ ID No 19) | GCTGCCTTGGGAGGCCTTGCGGCG GATCAGCCTGAAAATCATCAGGCT CTTGCAGAACCAGTTACGGGTGTG GGGGAAGCAGGAGTGTCCCCCGTC AACGAAGCTGGTGAGTCATACAGT TCTGCAACTTCGGGTGTCCAAGAA GCTACCGCCCCAGGTGCAGTGCTC CTGGACGCAATCGATGCCGAGTCG GATAAGGTGGACAATCAGGCGGAG GGAGGTGAGCGTATGAAGAAGGTC GAAGAGGAGTTGTCGTTATTGAGG CGGGAATTATATGATCGCACAGAT CGCCCTGGT | GRA 3 known | Dense granule protein—unknown as antigen in human response |
| Tx-1.11 (SEQ ID No 20) | CAGTTCGCTACCGCGGCCACCGCG TCAGATGACGAACTGATGAGTCGA ATCCGAAATTCTGACTTTTTCGAT GGTCAAGCACCCGTTGACAGTCTC AGACCGACGAACGCCGGTGTCGAC TCGAAAGGGACCGACGATCACCTC ACCACCAGCATGGATAAGGCATCT GTAGAGAGTCAGCTTCCGAGAAGA GAGCCATTGGAGACGGAGCCAGAT GAACAAGAAGAAGTTCAT | GRA 7 known T. gondii antigen | Dense granule protein |
| Tx-8.0 (SEQ ID No 21) | GAGAACCCGGTGAGACCGCCTCCT CCCGGTTTCCATCCAAGCGTTATT CCCAATCCCCCGTACCCGCTGGGC ACTCCAGCGGGCATGCCACAGCCA GAGGTTCC | GRA8 known T. gondii antigen | Dense granule protein |
| Tx-1.16 (SEQ ID No 22) | AGGAGGACTGGATGTCATGCCTTC AGGGAGAACTGCAGCCCTGGTAGA TGTATTGATGACGCCTCGCATGAG AATGGCTACACCTGCGAGTGCCCC ACAGGGTACTCACGTGAGGTGACT TCCAAGGCGGAGGAGTCGTGTGTG GAAGGAGTCGAAGTCACGCTGGCT GAGAAATGCGAGAAGGAATTCGGC ATCAGCGCGTCATCCTGCAAATGC GAT | MIC 3 | Microneme protein—unknown as antigen in human response |
| Tx-9.18 (SEQ ID No 23) | GCACCCACTCAATCTGAAATGAAA GAATTCCAAGAGGAAATCAAAGAA GGGGTGGAGGAAACAAAGCATGAA GACGATCCTGAGATGACGCGGCTC ATGGTGACCGAGAAGCAGGAGAGC AAAAATTTCAGCAAGATGGCGAAA TCCCAGAGTTTTAGCACGCGAATC GAAGAGCTCGGGGATCCATTTCG TTTCTAACTGAAACGGGGGTCACA ATGATCGAGTTGCCCAAAACTGTC AGTGAACATGACATGGACCAACTA CTCCAC | MIC 5 known T. gondii antigen | Microneme protein |
| Tx-7.11 (SEQ ID No 24) | GTTATGGCATCGGATCCCCCTCTT GTTGCCAATCAAGTTGTCACCTGC CCAGATAAAAAATCGACAGCCGCG GTCATTCTCACACCGACGGAGAAC CACTTCACTCTCAAGTGCCCTAAA ACAGCGCTCACAGAGCCTCCCACT CTTGCGTACTCACCCAACAGGCAA ATCTGCCCAGCGGGTACTACAAGT AGCTGTACATCAAAGCTGTAACAT TGAGCTCCTTGATTCCTGAAGCAG AAGATAGCTGGTGGACGGGGGATT CTGCTAGTCTCGACACGGCAGGCA TCAAACTCACAGTTCCAATCGAGA AGTTCCCCGTGACAACGCAGCGT TTGTGGTCGGTTGCATCAAGGGAG ACGACGCACAGAGTTGTATGGTCA CGGTGACAGTACAAGCCAGAGCCT CATCGGTCGTCAATAATGTCGCAA GGTGCTCCTATGGTCGGACAGC | SAG 1 known T. gondii antigen | Surface protein |
| Tx-4.18 (SEQ ID No 25) | CCATCGGTCGTCAATAATGTCGCA AGGTGCTCCTACGGTGCAGACAGC ACTCTTGGTCCTGTCAAGTTGTCT GCGGAAGGACCCACTACAATGACC CTCGTGTGCGGGAAAGATGGAGTC AAAGTTCCTCAAGACAACAATCAG TACTGTTCCGGGACGACGCTGACT GGTTGCAACGAGAAATCGTTCAAA GATATTTTGCCAAAATTAACTGAG AACCCGTGGCAGGGTAACGCTTCG AGTGATAAGGGTGCCACGCTAACG ATCAAGAAGGAAGCATTTCCAGCC GAGTCAAAAAGCGTCATTATTGGA TGCACAGGGGGATCGCCTGAGAAG CATCACTGTACCGTGAAACTGGAG TTTGCCGGGGCTGCAGGGTCAGCA AAATCGGCT | SAG 1 known T. gondii antigen | Surface protein |

The clone Tx-4.11 constitutes a fragment of the antigen GRA1 (Cesbron-Delauw et al., 1989, *Proc. Natl. Acad. Sci. USA* 86:7537–7541) but has never been identified as an "antigen fragment" of the protein in the human humoral response. Said clone has the amino acid sequence (SEQ ID No 26) SGGTGQGLGIGESVDLEMMGN-TYRVERPTGNPDLLKIMKASDGSY-SEVGNVNVEEVIDTMKSMQRDEDIFLR ALNKGETVEEAIEDVAQAEGLNSE-QTLQLEDAVSAVASVVQDE and its use as a fragment containing an epitope is covered by the present invention.

The clone TxM-17.2 constitutes a fragment of the antigen GRA2 (Prince et al., 1989, *Mol. Biochem. Parasitol.*, 34: 3–14) but has never been identified as an "antigen fragment" of the protein in the human humoral response. Said clone has the amino acid sequence (SEQ ID No 27) YSSPRIVVLIRY-CFFSTYRLTMFAVKHCLLVVAVGALVN-VSVRAAEFSGVVNQGP and its use a fragment containing an epitope is covered by the present invention.

The clone Tx-15.11 constitutes a fragment of the gene GRA3 (Bermudes et al., 1994, *Mol. Biochem. Parasitol.*, 68: 247–257) and has never been identified as an antigen in the human antibody response. Said clone has the amino acid sequence (SEQ ID No 28) AALGGLAADQPEN-HQALAEPVTGVGEAGVSPVNEAGESYSSATSG VQEATAPGAVLLDAIDAESDKVDNQAEG-GERMKKVEEELSLLRRE LYDRTDRPG and its use as a fragment containing an epitope is covered by the present invention.

The clone Tx-1.11 constitutes a fragment of the antigen GRA7 (Bonhomme et al., 1998, *J. Histochem. Cytochem.* 46, 1411–1421) and has never been identified as an "antigen fragment" of the protein in the human humoral response. Said clone has the amino acid sequence (SEQ ID No 29) FATAATASDDELMSRIRNSD-FFDGQAPVDSLRPTNAGVDSKGTD-DHLTTSMDKASVESQLPRREPLETEPDEQEEVHF and its use as a fragment containing an epitope is covered by the present invention.

The clone Tx-8.0 constitutes a fragment of the antigen GRA8 (Kimberly et al., 2000, *Mol. Biochem. Parasitol.*, 105: 25–37) and has never been identified as an "antigen fragment" of the protein in the human humoral response. Said clone has the amino acid sequence (SEQ ID No 30) ENPVRPPPPGFHPSVIPNPPYPLGTPAGMPQPEVP and its use as a fragment containing an epitope is covered by the present invention.

The clone Tx-1.16 constitutes a fragment of the gene MIC3 (Garcia-Réguet et al., 2000, *Cellular Microbiol.*, 2: 353–364) and has never been identified as an antigen in the human antibody response. Said clone has the amino acid sequence (SEQ ID No 31) RRTGCHAFRENCSPGRCID-DASHENGYTCECPTGYSREVTSKAEE-SCVEGVEVTLAEKCEKE FGISASSCKCD and its use as a fragment containing an epitope is covered by the present invention.

The clone Tx-9.18 constitutes a fragment of the antigen MIC5 (Brydges et al., 2000, *Mol. Biochem. Parasitol.*, 111: 51–66) but has never been identified as an "antigen fragment" of the protein in the human humoral response. Said clone has the amino acid sequence (SEQ ID No 32) APTQSEMKEFQEEIKEGVEETKHED-DPEMTRLMVTEKQESKNFSKMAKSQSF-STRIEELGGSISFLTETGVTMIELPKTVSEHDMDQLL H and its use as a fragment containing an epitope is covered by the present invention.

The clone Tx-7.11 constitutes a fragment of the antigen SAG1 (Burg et al., 1988, *J. Immunol.*, 141:3584–3591) but has never been identified as an "antigen fragment" of the protein in the human humoral response. Said clone has the amino acid sequence (SEQ ID No 33) VMASDPPLVANQV-VTCPDKKSTAAVILTPTENHFTLKCPK-TALTEPPTLAYSPNR QICPAGTTSSCTSKAVTLSSLIPE-AEDSWWTGDSASLDTAGIKLTVPI EKFPVTTQTFVVGCIKGDDAQSCM-VTVTVQARASSVVNNVARCSYG ADS and its use a fragment containing an epitope is covered by the present invention.

The clone Tx-4.18 constitutes a fragment of the antigen SAG1 (Burg et al., 1988, *J. Immunol.*, 141:3584–3591) but has never been identified as an "antigen fragment" of the protein in the human humoral response. Said clone has the amino acid sequence (SEQ ID No 34) PSVVNNVARC-SYGADSTLGPVKLSAEGPTT-MTLVCGKDGVKVPQDNNQYCSGTT LTGCNEKS-FKDILPKLTENPWQGNASSDKGATLTIKKEAFPAESKS VIIGCTGGSPEKHHCTVKLEFAGAAGSAKSA and its use as a fragment containing an epitope is covered by the present invention.

Expression of cDNA Fragments Selected from the Library as Fusion Products with GST The plasmid pGEX-SN was constructed by cloning the DNA fragment deriving from the hybridisation of the synthetic oligo-nucleotides K108 5'-GATCCTTACTAGTTT-TAGTAGCGGCCGCGGG-3' (SEQ ID No 35) and K109 5'-AATTCCCGCGGCCGCTACTAAAACTAGTAAG-3' (SEQ ID No 36) in the BamHI and EcoRI sites of plasmid pGEX-3X (Smith and Johnson, 1988, *Gene*, 67, 31–40).

The phage clones for which specific reactivity with sera of patients testing positive for *Toxoplasma gondii* was demonstrated, were amplified and then analysed with a substantial panel of positive and negative sera. After this ELISA study, DNA inserts of clones that showed multiple reactivity with *Toxoplasma gondii*-positive sera and presented no reactivity with the negative sera were cloned as fusion products with the protein Glutathione Sulphur Transferase (GST) and expressed in the cytoplasma of bacterial cells, for the purposes of determining their specificity and selectivity. To produce the fusion proteins each clone was amplified from a single phage plaque by PCR, using the following oligo-nucleotides: K47 5'-GGGCACTCGACCGGAATTATCG-3' (SEQ ID No 37) and K85 5'-GGGTAAAG-GTTTCTTTGCTCG-3' (SEQ ID No 38). The resulting fragment was then purified by means of the "Qiagen Purification Kit" (Qiagen, Calif., USA), digested with the restriction enzymes SpeI and NotI and cloned in the vector pGEX-SN to generate the fusion with GST. The corresponding recombinant proteins were then expressed in *E. coli* and purified by affinity using Glutathione-Sepharose resin (Amersham Pharmacia Biotech, Sweden) and following standard protocols (Sambrook et al., 1989, *Molecular Cloning*, Cold Spring Harbor Laboratory Press, Cold Spring Harbor).

The following table 3, by way of examples, presents the reactivity with negative and positive sera of a number of the clones selected, assayed in the form of fusion proteins:

TABLE 3

| Name of clone | Reactivity of GST fusion protein with positive sera (pos./total neg.) | Reactivity of GST fusion protein with negative sera (neg./total neg.) |
|---|---|---|
| Tx-4.11 | 32/40 | 1/28 |
| Tx-15.11 | 22/40 | 0/28 |
| Tx-1.11 | 27/40 | 0/28 |
| Tx-8.0 | 13/40 | 0/28 |
| Tx-1.16 | 31/40 | 0/28 |
| Tx-9.18 | 3/40 | 1/28 |
| Tx-7.11 | 39/40 | 3/28 |
| Tx-4.18 | 21/40 | 1/28 |

IgG Avidity for Determining the Time of Infection

Measurement of the binding force between immunoglobulin G (IgG) and the *T. gondii*-specific antigens (IgG avidity) is a diagnostic method used to establish the time of infection: IgG avidity is lower during the acute phase of the infection and then tends to increase in the course of time (Hedman et al. 1989 *J. Infect. Dis.* 159, 736–740). Evaluation of IgG avidity is based on an enzyme-linked immunosorbent assay (ELISA) in which the immunoglobulins are "detached" from the antigen by washing with a urea denaturing solution. A mathematical calculation based on the reactivity before and after the denaturing washing makes it possible to estimate serum IgG avidity (Jenum et al., 1997. *J. Clin. Microbiol.* 35, 1972–1977). To evaluate the antigenic properties of the protein fragments described in the present invention, an IgG avidity test based on recombinant antigen fragments was developed and the results obtained were compared with the assay performed with a commercial kit (Toxo-IgG avidity kit, bioMerièux, France) that employs the whole parasite extract as antigen.

For the avidity analysis 27 sera coming from women who contracted primary Toxoplasmosis during pregnancy and collected at different times after infection were used. The infection was diagnosed by seroconversion during gestation, taking into consideration last negative and first positive samples. For each sample the specific IgG and IgM levels for *T. gondii* and the IgG avidity were determined by means of the use of commercial kits (LDBIO Diagnostic, France; bioMerièux, France). Multi-well plates (Nunc, Denmark) were incubated overnight at 4° C. with a solution of NaHCO$_3$ 50 mM, pH 9.6 containing the antigen fragments expressed as GST fusion proteins at a final concentration of 5 µg/ml. The plates were blocked with 200 µl of blocking solution (5% skimmed milk powder in PBS, 0.05% Tween-20) and then washed 5 times with washing buffer (PBS, 0.05% tween-20). Serial dilutions of serum (1:50, 1:200, 1:800, 1:3200) in 100 µl of blocking solution were incubated on plates for 60 minutes at 37° C. The plates were then incubated with a denaturing solution of urea 6M in PBS/0.02% Tween-20 for 30 minutes at 37° C. In parallel, for every sample, the same dilutions of serum were effected and the wells concerned were incubated with normal washing buffer. 100 µl of blocking solution containing human anti-IgG antibodies conjugated with the enzyme alkaline phosphatase (diluted 1:10000) were added to the plates. After 30 minutes' incubation at 37° C. the plates were washed and the enzyme activity was determined with 100 µl of development solution (10% diethanolamine pH 9.8, 0.5 mM MgCl$_2$, 0.05% NaN$_3$) containing the reaction substrate p-nitrophenylphosphate (Sigma-Aldrich, USA). The enzyme activity was measured at optical densities of 405 nm and 620 nm by means of an automatic ELISA OD reader (Multiskan Labsystem, Finland) and the avidity calculation was done according to the mathematical analysis described in the literature (Jenum et al., 1997. *J. Clin. Microbiol.* 35, 1972–1977).

The following table 4 gives, by way of examples, the avidity of the human sera for a number of the antigen fragments selected.

The values should be interpreted as follows (commercial kit criterion):

<15% Low avidity: acute infection in the last three months

15%–30% Borderline avidity: probable primary infection within 3–6 months is possible >30% High avidity: excludes primary infection within the last three months

| Serum | Time from infection (months) | Commercial kit bioMerlèux | tx-15.11 | tx-1.11 | Clones-GST tx-8.0 | tx-4.18 | tx-7.11 | tx-1.16 |
|---|---|---|---|---|---|---|---|---|
| T1 | 1 | 7.8% | 20.0% | 6.9% | 12.0% | — | — | 24.0% |
| T2 | 1 | 5.7% | 7.9% | 2.3% | 10.0% | 9.8% | 7.9% | 2.7% |
| T3 | 1–2 | 2.5% | 5.4% | 6.3% | 9.5% | 8.7% | 11.5% | 1.0% |
| T4 | 1–2 | 8.1% | 4.5% | 9.0% | 4.0% | 10.3% | | 9.5% |
| T5 | 1–2 | 4.5% | 2.4% | 4.0% | 9.3% | 7.7% | 6.7% | 11.0% |
| T6 | 1–2 | 2.6% | 10.0% | 4.7% | 2.0% | 10.0% | 7.1% | 12.4% |
| T7 | 1–2 | 11.6% | 9.1% | 13.0% | 8.0% | 15.6% | 4.2% | 26.0% |
| T8 | 1–2 | 6% | 4.2% | 8.7% | 1.7% | 7.5% | 19.3% | 26.2% |
| T9 | 2–3 | 4.9% | 17.0% | 5.5% | 3.0% | 9.8% | 4.8% | 21.0% |
| T10 | 2–3 | 13.7% | 27.0% | | 14.5% | 28.1% | 4.8% | |
| T11 | 2–3 | | | | 15.7% | | | |
| T12 | 3–4 | 16.2% | 29.0% | 25.1% | 13.9% | | 8.6% | |
| T13 | 4–5 | | 20.1% | | — | — | 28.6% | |
| T14 | 4–5 | | 22.0% | | | | | |
| T15 | 5–6 | 14.7% | | 9.5% | 14.6% | | 8.3% | |
| T16 | 6 | | | | | — | | |
| T17 | 6 | | — | — | — | | 10.2% | |
| T18 | 6–7 | | | | — | | | |
| T19 | 6–7 | | | 23.0% | | 24.6% | | |
| T20 | 7–8 | | | | | | | |
| T21 | 7–8 | | 22.0% | | 16.4% | | | |
| T22 | 7–8 | 26.2% | 2.5% | — | 9.0% | | | |
| T23 | 8 | | | | — | — | 21.0% | |
| T24 | 8 | | 26.5% | 22.4% | | | 16.7% | |
| T25 | 10 | | | | | | 23.2% | |
| T26 | 24 | 25.6% | | | — | — | | |
| T27 | 38 | | 25.0% | | | | | |

EXAMPLE 2

Using the vector λKM4 of Example 1, a library of DNA fragments of known *Toxoplasma gondii* genes was constructed.

Cells of *Toxoplasma gondii* (10$^6$ parasites, strain ME49) were grown in vitro in monkey kidney cells ("VERO" African green monkey cells) using DMEM culture medium containing 10% foetal bovine serum, 2 mM glutamine and 0.05 mg/ml gentamicin (Gibco BRL, Canada). To have both forms of the parasite (tachyzoites and bradyzoites) present in the cell cultures, an experimental protocol was used based on the change in pH of the culture medium (Soete et al., 1994, *Experimental Parasitology*, 78, 361–370). The parasites were collected after complete lysis of the host cells and purified by filtration (filter porosity 3 µm) followed by centrifuging. 2 µg of mRNA were isolated from 5×10$^6$ parasites using the "QuickPrep Micro mRNA Purification Kit" (Amersham Pharmacia Biotech, Sweden) and following the manufacturer's instructions. cDNA was synthesised from 200 ng of poly(A)+ RNA using the "SMART cDNA Library Construction Kit" (Clontech, CA, USA) and following the manufacturer's instructions. Genomic DNA was purified from the remaining 5×10$^6$ cells using standard procedures (Sambrook et al., 1989, *Molecular Cloning: a laboratory manual*, Cold Spring Harbor Laboratory Press, NY) and stored at −20° C.

For the construction of the expression/exposure library the following genes, expressed only in the bradyzoite stage, were amplified by means of PCR with specific oligonucleotides:

1—SAG2D (Lekutis et al., 2000, *Experimental Parasitology*, 96, 89–96) was obtained from genomic DNA using the oligonucleotides 5'-ATGGCGGCTGCACACTCG-3' (SEQ ID No 39) and 5'-GAACATATTCCCTGTCAC-CAATG-3' (SEQ ID No 40);

2—SAG4 (Odberg-Ferragut et al., 1996, *Molecular and Biochemical Parasitology*, 82, 237–244) was obtained from genomic DNA using the oligonucleotides 5'-AT-GACGAAAAATAAAATTCTTCTC-3' (SEQ ID No 41) and 5'-CATTGATATCAACACAAAGGCC-3' (SEQ ID No 42)

3—BSR4 (Manger et al., 1998, *Infection and Immunity*, 66, 2237–2244) was obtained from genomic DNA using the oligonucleotides 5'-ATGGTGATGATGGGCAGCATG-3' (SEQ ID No 43) and 5'-CGGCGGCCGCGCTAGAGG-3' (SEQ ID No 44);

4—MAG1 (Parmley et al., 1994, *Molecular and Biochemical Parasitology*, 66, 283–296) was obtained from genomic DNA using the oligonucleotides 5'-CGTTG-GATCCTTGGATTGAGCCAAAGGGTGCCAG-3' (SEQ ID No 45) and 5'-CCCAGAATTCTCAAGCTGC-CTGTTCCGCTAAGATCTG-3' (SEQ ID No 46);

5—LDH2 (Yang and Parmley, 1997, *Gene*, 184, 1–12) was obtained from cDNA using the oligonucleotides 5'-AT-GACGGGTACCGTTAGCA-G-3' (SEQ ID No 47) and 5'-ACCCAGCGCCGCTAAACTC-3' (SEQ ID No 48);

6—ENO1 (Dzierszinski et al., 2001, *Journal of Molecular Biology*, 309, 1017–1027) was obtained from genomic DNA using the oligonucleotides 5'-ATGGTGGTTAT-CAAGGACATCG-3' (SEQ ID No 49) and 5'-TTTTGGGTGTCGAAAGCTCTC-3' (SEQ ID No 50);

7—BAG1 (Bohne et al., 1995, *Molecular Microbiology*, 16, 1221–1230) was obtained from cDNA using the oligonucleotides 5'-ATGGCGCCGTCAGCATCG-3' (SEQ ID No 51) and 5'-CTTCACGCTGATTTGTTGCTTTG-3' (SEQ ID No 52);

8—p-ATPase (Holpert et al., 2001, Molecular and Biochemical Parasitology, 112, 293–296) was obtained from genomic DNA using the oligonucleotides 5'-ATGGAC-GAAGCGAGCAGAAGG-3' (SEQ ID No 53) and 5'-ACGCGTGATCGAAGGAACCG-3' (SEQ ID No 54).

10 µg of DNA deriving from a mixture of the amplification products of the above-mentioned genes were fragmented randomly using 0.5 ng of the endonuclease DNaseI (Sigma-Aldrich, USA). The mixture of DNA and DNaseI was incubated for 20 minutes at 15° C. and the DNA fragments were purified by means of the "QIAquick PCR Purification Kit" (Qiagen, Calif., USA), following the manufacturer's instructions. The 3 µg ends of the cDNA fragments were "flattened" by incubating the DNA with 9 units of the enzyme T4 DNA polymerase (New England Biolabs, MA, USA) for 60 minutes at 15° C. The fragments were then purified by means of extraction in phenol/chloroform and subsequent precipitation in ethanol. 500 ng of the resulting DNA were bound with a 20-fold molar excess of "synthetic adaptors" for the purposes of adding the restriction sites SpeI and NotI to the ends of the fragments. Six adaptors were used, obtained by hybridisation of the following pairs of oligonucleotides: K185 5'-CTAGTCGTGCTGGC-CAGC-3' (SEQ ID No 5) and K186 5'-GCTGGCCAG-CACGA-3' (SEQ ID No 6); K187 5'-CTAGTCGTGCTG-GCCA GCT-3' (SEQ ID No 7) and K188 5'-AGCTGGCCAGCACGA-3' (SEQ ID No 8); K189 5'-CTAGTCGT GCTGGCCAGCTG-3'(SEQ ID No 9) and K190 5'-CAGCTGGCCAGCACGA-3' (SEQ ID No 10); K191 5'-TCTGGTGGCGGTAGC-3' (SEQ ID No 11) and K192 5'-GGCCGCTACCGCCACCAGA-3'(SEQ ID No 12); K193 5'-TTCTGGTGGCGGTAGC-3' (SEQ ID No 13) and K194 5'-GGCCGCTACCGCCACCAGAA-3' (SEQ ID No 14); K195 5'-TTTCTGGTGGCGGTAGC-3' SEQ ID No 15) and K196 5'-GGCCGCTACCGCCACCAGAAA-3' (SEQ ID No 16). The excess of unligated adaptors was removed from the ligation mixture by electropheresis on 2% agarose gel and the cDNA fragments with molecular weights ranging from 250 bp to 1000 bp were excised from the gel and purified by means of the "Qiaquick gel extraction kit" (Qiagen, Calif., USA) following the manufacturer's instructions. The vector λKM4 was digested with SpeI/NotI and for the construction of the library 6 ligation mixtures were performed, each containing 0.4 µg of vector and approximately 7 ng of insert. After overnight incubation at 4° C. the ligation mixtures were packaged in vitro with the "Ready-To-Go lambda packaging kit" (Amersham Pharmacia Biotech, Sweden) and plated for infection of BB4 cells (bacterial cells of *E. coli* strain BB4; Sambrook et al., 1989, *Molecular Cloning: a laboratory manual*, Cold Spring Harbor Laboratory Press, NY). After overnight incubation at 37° C. the phage was eluted from the plates with SM buffer (Sambrook et al., 1989, *Molecular Cloning: a laboratory manual*, Cold Spring Harbor Laboratory Press, NY), purified, concentrated and stored at −80° C. in SM buffer containing 7% dimethylsulphoxide. The complexity of the library calculated as the number of total independent clones with inserts was $10^6$ clones.

Affinity selection, phage-ELISA, immunoscreening and phage clones preparation were performed exactly as described in Example 1.

The following table 5 gives, by way of examples, the reactivity of a number of the recombinant bacteriophages selected.

TABLE 5

| Name of clone | Reactivity of phage clone with positive sera (positive/total positive) | Reactivity of phage clone with negative sera (negative/total negative) |
| --- | --- | --- |
| TxB-cl21.2 | 10/20 | 1/10 |
| TxB-cl26.3 | 12/20 | 0/10 |
| TxB-44.3 | 10/20 | 0/10 |
| TxB-7.1 | 8/20 | 0/10 |
| TxB-9.1 | 1/20 | 1/10 |
| TxB-12.1 | 5/20 | 0/10 |

Characterisation of Positive Clones

The clones which showed multiple reactivity with the *Toxoplasma gondii* positive sera and which presented no reactivity with the negative sera were subsequently sequenced and compared with the sequences of the genes used to construct the library.

The following table 6 gives, by way of examples, the sequences of some of the clones selected:

TABLE 6

| Name of clone | Sequence |
| --- | --- |
| TxB-26.3 (SEQ ID No 55) | GGATTGAGCCAAAGGGTGCCAGAGCTACCAGAAGT GGAGCCCTTTGATGAAGTAGGCACGGGAGCTCGAC GGTCCGGGTCCATTGCGACCCTTCTTCCACAAGAC GCTGTTTTATATGAGAACTCAGAGGACGTTGCCGT TCCGAGTGATTCAGCATCGACCCCGTCATACTTTC ATGTGGAATCTCCAAGTGCTAGTGTGGAAGCCGCG ACTGCCGCTGTGGGAGAGGTGGTGCCGGACTGTGA |

TABLE 6-continued

| Name of clone | Sequence |
|---|---|
| | AGAACAACAGGAACAGGGTGACACGACGTTATCCG<br>ATCACGATTTCCATTCA |
| TxB-cl7.1<br>(SEQ ID No 56) | TCTTCAGAAAGATGACGTAACCATAGAAGTCGACA<br>ACGGAGCCATCGTTATCAAAGGAGAGAAGACCTCG<br>AAAGAAGCGGAGAAAGTGGACGATGGCAAAACAAA<br>GAACATTTTGACTGAGCGAGTGTCCGGTTATTTTG<br>CGCGCCGGTTCCAGCTCCCGAGTAATTACAAGCCC<br>GACGGAATCAGTGCGGCAATGGACAACGGCGTTCT<br>ACGTGTCACGATCAAGGTCGAGGATTCAGGGGGCG<br>CAAAGCAACAAATCAGCGTG |

The clone TxB-cl26.3 constitutes a fragment of the gene MAG1, a 65 kDa protein of the matrix and wall of *T. gondii* cysts (Parmley et al., 1994, *Molecular and Biochemical Parasitology*, 66, 283–296), the protein product of which has never been identified as an "antigen fragment" in the human humoral response. Said clone has the amino acid sequence GLSQRVPELPEVEPFDEVGTGARRSGSI-ATLLPQDAVLYENSEDVAVPSDSAS-TPSYFHVESPSASVEAATGAVGEVVPDCEE QQEQGDTTLSDHDFH (SEQ ID No 57) and its use as a fragment containing an epitope is covered by the present invention.

The clone TxB-cl7.1 constitutes a fragment of the gene BAG1, a 30 kDa protein of the heat shock protein family of *T. gondii* (Bohne et al., 1995, *Molecular Microbiology*, 16, 1221–1230), the protein product of which has never been identified as an "antigen fragment" in the human humoral response. Said clone has the amino acid sequence LNPID-DMLFETALTANEMMEDITWRPRVDVEFD-SKKKEMIILADLP GLQKDDVTIEVDNGAI-VIKGEKTSKEAEKVDDGKTKNILTERVSGY FARRFQLPSNYKPDGISAAMDNGVLRV-TIKVEDSGGAKQQISV (SEQ ID No 58) and its use as a fragment containing an epitope is covered by the present invention.

Expression of DNA Fragments Selected from the Library as Fusion Products with GST The phage clones for which specific reactivity with sera of patients testing positive for *Toxoplasma gondii* was demonstrated, were amplified and then analysed with a substantial panel of positive and negative sera. After this ELISA study, the clones that showed multiple reactivity with *Toxoplasma gondii*-positive sera and presented no reactivity with the negative sera were cloned as fusion products with the protein Glutathione Sulphur Transferase (GST) and expressed in bacterial cells, for the purposes of determining their specificity and selectivity. To produce the fusion proteins each clone was amplified from a single phage plaque by PCR, using the following oligonucleotides: K47 5'-GGGCACTCGACCGGAATTATCG-3' (SEQ ID No 37) and K85 5'-GGGTAAAGGTTTCTTTGCTCG-3' (SEQ ID No 38). The resulting fragment was then purified by means of the "Qiagen Purification Kit" (Qiagen, Calif., USA), digested with the restriction enzymes SpeI and NotI and cloned in the vector pGEX-SN to generate the fusion with GST. The corresponding recombinant proteins were then expressed in *E. coli* and purified by affinity using Glutathione-Sepharose resin (Amersham Pharmacia Biotech, Sweden) and following standard protocols (Sambrook et al., 1989, *Molecular Cloning*, Cold Spring Harbor Laboratory Press, Cold Spring Harbor).

The following table 7, by way of examples, presents the reactivity with negative and positive sera of a number of the clones selected, assayed in the form of fusion proteins:

TABLE 7

| Name of clone | Reactivity of GST fusion protein with positive sera (pos./total neg.) | Reactivity of GST fusion portein with negative sera (neg./totale neg.) |
|---|---|---|
| TxB-cl26.3 | 30/34 | 0/32 |
| TxB-cl7.1 | 17/34 | 0/32 |

EXAMPLE 3

By using the same strategy described in Example 2, a gene collection of DNA encoding for protein products of the *Toxoplasma gondii* microneme family was used to construct a "microneme-display library".

For the construction of the microneme-library the following genes were amplified by means of PCR with specific oligonucleotides:

1—MIC2 (Wan et al, 1997, *Mol. Biochem. Parasitol.* 84: 203–214) was obtained from single strand cDNA using the oligonucleotides 5'-ATGAGACTCCAACCGAG-GCC-3' (SEQ ID No 69) and 5'-CTGCCT-GACTCTTTCTTGGACTG-3' (SEQ ID No 70);

2—M2AP (Rabenau et al., 2001, *Mol. Microbiol.* 41: 537–547) was obtained from single strand cDNA using the oligonucleotides 5'-GGAAAGTTGGAAATCCG-GCGGC-3' (SEQ ID No 71) and 5'-CGCCTCATCGT-CACTCGGC-3' (SEQ ID No 72)

3—MIC4 (Brecht et al., 2001, *J. Biol. Chem.* 276:4119–412) was obtained from single strand cDNA using the oligonucleotides 5'-ATGAGAGCGTCGCTCCCGG-3' (SEQ ID No 73) and 5'-GTGTCTTTCGCTTCAAGCACCTG-3' (SEQ ID No 74);

4—AMA1 (Hehl et al., 2000, *Infect. Immun.* 68:7078–7086) was obtained from single strand cDNA using the oligonucleotides 5'-ATGGGGCTCGTGGGCGTAC-3' (SEQ ID No 75) and 5'-GATCAACGCAGTGTTAGAGCCAC-3' (SEQ ID No 76);

10 µg of DNA deriving from a mixture of the amplification products of the above-mentioned genes were fragmented randomly using 0.5 ng of the endonuclease DNaseI (Sigma-Aldrich, USA). The mixture of DNA and DNaseI was incubated for 20 minutes at 15° C. and the DNA fragments were purified by means of the "QIAquick PCR Purification Kit" (Qiagen, Calif., USA), following the manufacturer's instructions. Consequent steps for the construction of the microneme-library, and for the affinity selection were performed by following the procedure described in Example 2.

Selection of the Microneme-Library with Sera of Infants Who Were Infected by *T. gondii* During Pregnancy To identify the antigenic domains of the *T. gondii* microneme proteins an affinity selection procedure was used consisting of two "panning" cycles with four sera collected from infants who were congenitally infected by the parasite, followed by an immunological screening procedure carried out with the same sera. The library was selected with sera T1, T2, T3, T4, generating, after a single selection cycle, the corresponding mixtures p1$^I$, p2$^I$, p3$^I$ and p4$^I$. Each mixture was then subjected to a second affinity selection cycle with the same serum, giving rise to a second series of mixtures (called p1$^{II}$p2$^{II}$, p3$^{II}$ and p4$^{II}$). Various positive clones were identified by means of immunoplate screening per plaque of reactive mixtures.

Phage-Elisa, immunoscreening, and the preparation of phage clones were subsequently performed exactly as described in Examples 1 and 2.

The following table 8 gives, by way of examples, the reactivity of a number of the recombinant bacteriophages selected.

TABLE 8

| Name of clone | Reactivity of phage clone with positive sera (positive/ total positive) | Reactivity of phage clone with negative sera (negative/ total negative) |
| --- | --- | --- |
| Tx-2.a | 13/16 | 0/10 |
| Tx-1.b | 11/16 | 0/10 |
| Tx-11.b | 12/16 | 0/10 |
| Tx-13.b | 9/16 | 0/10 |
| Tx-15.b | 9/16 | 0/10 |

Characterisation of Positive Clones

The following table 9 gives the sequences of the clones selected:

TABLE 9

| Name of the clone | Sequence | Identification | Classification |
| --- | --- | --- | --- |
| Tx-2.a (SEQ ID No 59) | CCCCAGGATGCCATTTGCTCGGATT GGTCCGCATGGAGCCCCTGCAGTGT ATCCTGCGGTGACGGAAGCCAAATC AGGACGCGAACTGAGGTTTCTGCTC CGCAACCTGGAACACCAACATGTCC GGACTGCCCTGCGCCCATGGGAAGG ACTTGCGTGGAACAAGGCGGACTTG AAGAAATCCGTGAATGCAGTGCGGG GGTATGTGCTGTTGACGCTGGATGT GGCGTCTGGGTT | MIC2 | Microneme protein unknown as antigen in human response |
| Tx-1.b (SEQ ID No 60) | CCGTGTCCAATTAATGCAACTTGCG GTCAGTTTGAAGAATGGAGTACATG CTCGGTCTCATGTGGTGGTGGACTG AAAACGAGGTCGAGGAACCCTTGGA ATGAAGACCAACAACATGGAGGACT ATCCTGCGAGCAGCAGCCATCCTGGT GGGCGGACGGAAACGGTAACTTGCA ATCCTCAAGCGTGTCCTGTGGATGA ACGACCGGGGAGTGGGCAGAGTGG GGGGAATGTAGTGTCACGTGCGGCG ACGGAGTGCGAGAGCGCAGGCGCGG GAAAAGTCTAGTTGAGGCTAAATTC GGCGGACGCACCATTGATCAGCAGA ATGAGGCTCTTCCGGAAGACTTAAA AATCAAAAACGTCGAGTATGAGCCA TGTTCGTATCCTGCTTGTGGAGCTT CCTGCACGTACGTCTGGAGTGACTG GAACAAG | MIC2 | Microneme protein unknown as antigen in human response |
| Tx-11.b (SEQ ID No 61) | AACGAACCGGTGGCCCTAGCTCAGC TCAGCACATTCCTCGAGCTCGTCGA GGTGCCATGTAACTCTGTTCATGTT CAGGGGGTGATGACCCCGAATCAAA TGGTCAAAGTGACTGGTGCAGGATG GGATAATGGCGTTCTCGAGTTCTAT GTCACGAGGCCAACGAAGACAGGCG GGGACACAAGCCGAAGCCATCTTGC GTCGATCATGTGTTATTCCAAGGAC ATTGACGGCGTGCCGTCAGACAAAG CGGGAAAGTGCTTTCTGAAGAACTT TTCTGGTGAAGACTCGTCGGAAATA GACGAAAAAGAAGTATCTCTACCCA TCAAGAGCCACAACGATGCGTTCAT GTTCGTTTGTTCTTCAAATGATGGA TCCGCACTCCAGTGTGATGTTTTCG CCCTTGATAACACCAACTCTAGCGA CGGGTGGAAAGTGAATACCGTGGAT CTTGGCGTCAGCGTTAGTCCGGATT TGGCATTCGGACTCACTGCAGATGG GGTCAAGGTGAAGAAGTTGTACGCA | M2AP | Microneme protein unknown as antigen in human response |

TABLE 9-continued

| Name of the clone | Sequence | Identification | Classification |
| --- | --- | --- | --- |
| | AGCAGCGGCCTGACAGCGATCAACG ACGACCCTTCCTTGGGGTGCAAGGC TCCTCCCCATTCTCCGCCGGCCGGA GAGGAACCGAGTTTGCCGTCGCCTG AAAACAGCGGGTCTGCAACACCAGC GGAAGAAAGTCCGTCTGAGTCTGAA TCT | | |
| Tx-13.b (SEQ ID No 62) | CTTCGCGGGTACAGGTTCGGTGTTT GGAAGAAAGGCCGTTGCCTCGACTA CACTGAATTGACCGACACTGTGATA GAACGTGTTGAGTCAAAGGCACAGT GCTGGGTGAAAACCTTTGAAAACGA CGGGGTCGCGAGTGACCAACCCCAT ACGTATCCACTGACGTCGCAAGCAT CATGGAACGATTGGTGGCCTCTCCA CCAGAGTGACCAACCTCACTCAGGT GGCGTTGGGCGTAATTACGGTTTCT ACTACGTGGACACGACTGGAGAGGG CAAGTGTGCACTCTCTGACCAGGTA CCCGACTGCCTGGTGTCGGATTCTG CCGCCGTGTCGTATACAGCAGCGGG GAGTTTGTCTGAAGAGACGCCGAAT TTCATAATTCCGTCAAATCCCTCTG TTACTCCGCCAACGCCCGAGACGGC ACTTCAGTGCACGGCCGACAAGTTC CCCGACTCTTTCGGTGCCTGCGACG TTCAAGCGTGTAAAAGACAGAAGAC GTCCTGCGTTGGCGGACAGATTCAA AGTACTAGCGTCGACTGCACCGCGG ACGAACAAAATGAATGTGGCTCTAA CACTGCG | AMA1 | Microneme protein unknown as antigen in human response |
| Tx15.b (SEQ ID No 63) | AGTGCCAACGTAACAAGTTCGGAGC CTGCAAAACTTGATCTCTCTTGTGC GCACTCTGACAATAAGGGATCAAGG GCTCCCACAATAGGCGAGCCAGTGC CAGATGTGTCCCTGGAACAATGTGC TGCGCAATGCAAGGCTGTTGATGGC TGCACACATTTCACTTATAATGACG ATTCGAAGATGTGCCATGTGAAGGA GGGAAAACCCGATTTATACGATCTC ACAGGAGGCAAAACAGCACCGCGCA GTTGCGATAGATCATGCTTCGAACA ACACGTATCGTATGAGGGAGCTCCT GACGTGATGACAGCGATGGTCACGA GCCAGTCAGCGGACTGTCAGGCTGC GTGTGCGGCTGACCCGAGCTGCGAG ATCTTCACTTATAACGAACACGACC AGAAATGTACTTTCAAAGGAAGGGG GTTTTCTGCGTTTAAGGAACGAGGG GTGTTGGGTGTGACTTCCGGCCGA AACAGTTCTGCGATGAAGGCGGTAA ATTAACT | MIC4 | Microneme protein-unknown as antigen in human response |

The clones Tx-2.a e Tx-1.b represent two distinct fragments of the MIC2 gene (Wan et al, 1997, *Mol. Biochem. Parasitol.* 84: 203–214) and have never been identified as antigens of the human antibody response. Said clones have respectively the amino acid sequences PQDAICSDWSAW-SPCSVSCGDGSQIRTRTEVSAPQPGTPTCPDCPA PMGRTCVEQGGLEEIRECSAGVCAVDAGCGVWV (SEQ ID No 64) and PCPINATCGQFEEWSTCS-VSCGGGLKTRSRNPWNEDQQHGGLSCE QQHPG-GRTETVTCNPQACPVDER-PGEWAEWGECSVTCGDGVRER RRGKSLVEAKFG-GRTIDQQNEALPEDLKIKNVEYEPCSYPACGASC TYVWSDWNK (SEQ ID No 65) and their use as fragments containing an epitope is covered by the present invention.

The clone Tx-11.b represents a distinct fragment of the M2AP gene (Rabenau et al., 2001, *Mol. Microbiol.* 41:

537–547) and has never been identified as antigen of the human antibody response. Said clone has the amino acid sequence NEPVALAQLSTFLELVEVPCNSVH-VQGVMTPNQMVKVTGAGWDNGVLE-FYVTRPTKTGGDTSRSHLASIMCYSK DIDGVPSDK-AGKCFLKNFSGEDSSEIDEKEVSLPIKSHNDAFMFVC SSNDGSALQCDVFALDNTNSSDG-WKVNTVDLGVSVSPDLAFGLTA DGVKV YASSGL-TAINDDPSLGCKAPPHSPPAGEEPSLPSPENS GSAT-PAEESPSESES (SEQ ID No 66) and its use as fragment containing an epitope is covered by the present invention.

The clone Tx-13.b represents a fragment of the AMA1 gene (Hehl et al., 2000, *Infect. Immun.* 68:7078–7086). Said clone has the amino acid sequence LRGYRFGVWKKGR-CLDYTELTDTVIERVESKAQCWVKT-FENDGVASDQPHTYPLTSQASWNDWWPL-HQSDQPHSGGVGRNYG FYYVDTTGEGKCALSDQVPDCLVSD-SAAVSYTAAGSLSEETPNFIIP SNPSVTPPTPE-TALQCTADKFPDSFGACDVQACKRQKTSCVGGQIQ STSVDCTADEQNECGSNTA (SEQ ID No 67) and its use as fragment containing an epitope is covered by the present invention.

The clone Tx-15.b represents a fragment of the MIC4 gene (Brecht et al., 2001, J. Biol. Chem. 276:4119–4127). Said clone has the amino acid sequence SANVTSSEPAK-LDLSCAHSDNKGSRAPTIGEPVPD-VSLEQCAAQCKAVDGCTHFTYNDDSKM-CHVKEGKPDLYDLTGGKTAPRS CDRSCFEQHVSYEGAPDVMTAM-VTSQSADCQAACAADPSCEIFTY NEHDQKCT-FKGRGFSAFKERGVLGVTSGPKQFCDEGGKLT (SEQ ID No 68) and its use as fragment containing an epitope is covered by the present invention.

Expression of DNA Fragments Selected from the Microneme-Library as Fusion Products with GST Phage clones isolated from the microneme-library were cloned as fusion products with GST protein and expressed in bacterial cells, for the purposes of determining their specificity and selectivity. The procedure described in Examples 1 and 2 was used to produce the fusion proteins.

The following table 10, by way of example, presents the reactivity with negative and positive sera of a number of the clones selected, assayed in the form of fusion proteins:

TABLE 10

| Name of clone | Reactivity of GST fusion protein with positive sera (pos./total neg.) | Reactivity of GST fusion portein with negative sera (neg./totale neg.) |
|---|---|---|
| Tx-2.a | 29/30 | 0/15 |
| Tx-1.b | 15/30 | 0/15 |
| Tx-11.b | 23/30 | 0/15 |
| Tx-13.b | 24/30 | 0/15 |
| Tx-15.b | 12/30 | 0/15 |

The invention claimed is:

1. An isolated polypeptide consisting of an amino acid sequence selected from the group consisting of SEQ ID NOs: 31, 58, 26, 28, 29, 64, 65, 67, 66, 57, 34, 33, 32, 68, 30 and 27.

2. A pharmaceutical composition comprising a polypeptide of claim 1.

3. An isolated polypeptide consisting of the amino acid sequence of SEQ ID NO:26.

4. A composition comprising the polypeptide of claim 3.

* * * * *

SEQUENCE LISTING

<160> NUMBER OF SEQ ID NOS: 76

<210> SEQ ID NO 1
<211> LENGTH: 48
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
tttatctaga cccagcccta ggaagcttct cctgagtagg acaaatcc 48

<210> SEQ ID NO 2
<211> LENGTH: 32
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
gggtctagat aaaacgaaag gcccagtctt tc 32

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 3

```
ccgccttcca tgggtactag ttttaaatgc ggccgcacga gcaaagaaac ctttac        56
```

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4

```
agcttcctag ggctgggtct ag                                            22
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5

```
ctagtcgtgc tggccagc                                                 18
```

<210> SEQ ID NO 6
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6

```
gctggccagc acga                                                     14
```

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7

```
ctagtcgtgc tggccagct                                                19
```

<210> SEQ ID NO 8
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8

```
agctggccag cacga                                                    15
```

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 9

```
ctagtcgtgc tggccagctg                                               20
```

<210> SEQ ID NO 10
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 10
cagctggcca gcacga                                                    16

<210> SEQ ID NO 11
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 11
tctggtggcg gtagc                                                     15

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 12
ggccgctacc gccaccaga                                                 19

<210> SEQ ID NO 13
<211> LENGTH: 16
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 13
ttctggtggc ggtagc                                                    16

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 14
ggccgctacc gccaccagaa                                                20

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 15
tttctggtgg cggtagc                                                   17

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
ggccgctacc gccaccagaa a                                              21

<210> SEQ ID NO 17
<211> LENGTH: 348
<212> TYPE: DNA
<213> ORGANISM: Toxoplasma gondii

<400> SEQUENCE: 17
agtggaggga cagggcaggg attaggaatc ggagaatctg tagatttgga gatgatgggg    60
aacacgtatc gtgtggagag acccacaggc aacccggact tgctcaagat cgccattaaa   120
gcttcagatg gatcgtacag cgaagtcggc aatgttaacg tggaggaggt gattgatact   180
atgaaaagca tgcagaggga cgaggacatt tccttcgtg cgttgaacaa aggcgaaaca    240
gtagaggaag cgatcgaaga cgtggctcaa gcagaagggc ttaattcgga gcaaaccctg   300
caactggaag atgcagtgag cgcggtggcg tctgttgttc aagacgag                348

<210> SEQ ID NO 18
<211> LENGTH: 165
<212> TYPE: DNA
<213> ORGANISM: Toxoplasma gondii

<400> SEQUENCE: 18
tactcttcac cacgaatagt tgttttgatt agatattgct tcttctccac atatcgcctc    60
acaatgttcg ccgtaaaaca ttgtttgctg gttgttgccg ttggcgccct ggtcaacgtc   120
tcggtgaggg ctgccgagtt ttccggagtt gttaaccagg gacct                   165

<210> SEQ ID NO 19
<211> LENGTH: 297
<212> TYPE: DNA
<213> ORGANISM: Toxoplasma gondii

<400> SEQUENCE: 19
gctgccttgg gaggccttgc ggcggatcag cctgaaaatc atcaggctct tgcagaacca    60
gttacgggtg tgggggaagc aggagtgtcc cccgtcaacg aagctggtga gtcatacagt   120
tctgcaactt cggtgtgcca agaagctacc gccccaggtg cagtgctcct ggacgcaatc   180
gatgccgagt cggataaggt ggacaatcag gcggaggag gtgagcgtat aagaaggtc    240 gaagaggagt tgtcgttatt gaggcgggaa ttatatgatc gcacagatcg ccctggt     297

<210> SEQ ID NO 20
<211> LENGTH: 234
<212> TYPE: DNA
<213> ORGANISM: Toxoplasma gondii

<400> SEQUENCE: 20
cagttcgcta ccgcggccac cgcgtcagat gacgaactga tgagtcgaat ccgaaattct    60 gacttttcg atggtcaagc acccgttgac agtctcagac cgacgaacgc cggtgtcgac   120
tcgaaaggga ccgacgatca cctcaccacc agcatggata aggcatctgt agagagtcag   180

| cttccgagaa gagagccatt ggagacggag ccagatgaac aagaagaagt tcat | 234 |

<210> SEQ ID NO 21
<211> LENGTH: 104
<212> TYPE: DNA
<213> ORGANISM: Toxoplasma gondii

<400> SEQUENCE: 21

| gagaacccgg tgagaccgcc tcctcccggt ttccatccaa gcgttattcc caatcccccg | 60 |
| tacccgctgg gcactccagc gggcatgcca cagccagagg ttcc | 104 |

<210> SEQ ID NO 22
<211> LENGTH: 219
<212> TYPE: DNA
<213> ORGANISM: Toxoplasma gondii

<400> SEQUENCE: 22

| aggaggactg gatgtcatgc cttcagggag aactgcagcc ctggtagatg tattgatgac | 60 |
| gcctcgcatg agaatggcta cacctgcgag tgccccacag ggtactcacg tgaggtgact | 120 |
| tccaaggcgg aggagtcgtg tgtggaagga gtcgaagtca cgctggctga gaaatgcgag | 180 |
| aaggaattcg gcatcagcgc gtcatcctgc aaatgcgat | 219 |

<210> SEQ ID NO 23
<211> LENGTH: 270
<212> TYPE: DNA
<213> ORGANISM: Toxoplasma gondii

<400> SEQUENCE: 23

| gcacccactc aatctgaaat gaaagaattc caagaggaaa tcaaagaagg ggtggaggaa | 60 |
| acaaagcatg aagacgatcc tgagatgacg cggctcatgg tgaccgagaa gcaggagagc | 120 |
| aaaaatttca gcaagatggc gaaatcccag agttttagca cgcgaatcga agagctcggg | 180 |
| ggatccattt cgtttctaac tgaaacgggg gtcacaatga tcgagttgcc caaaactgtc | 240 |
| agtgaacatg acatggacca actactccac | 270 |

<210> SEQ ID NO 24
<211> LENGTH: 456
<212> TYPE: DNA
<213> ORGANISM: Toxoplasma gondii

<400> SEQUENCE: 24

| gttatggcat cggatccccc tcttgttgcc aatcaagttg tcacctgccc agataaaaaa | 60 |
| tcgacagccg cggtcattct cacaccgacg gagaaccact tcactctcaa gtgccctaaa | 120 |
| acagcgctca cagagcctcc cactcttgcg tactcaccca caggcaaat ctgcccagcg | 180 |
| ggtactacaa gtagctgtac atcaaaggct gtaacattga gctccttgat tcctgaagca | 240 |
| gaagatagct ggtggacggg ggattctgct agtctcgaca cggcaggcat caaactcaca | 300 |
| gttccaatcg agaagttccc cgtgacaacg cagacgtttg tggtcggttg catcaaggga | 360 |
| gacgacgcac agagttgtat ggtcacggtg acagtacaag ccagagcctc atcggtcgtc | 420 |
| aataatgtcg caaggtgctc ctatggtgcg gacagc | 456 |

<210> SEQ ID NO 25
<211> LENGTH: 393
<212> TYPE: DNA
<213> ORGANISM: Toxoplasma gondii

<400> SEQUENCE: 25

-continued

```
ccatcggtcg tcaataatgt cgcaaggtgc tcctacggtg cagacagcac tcttggtcct    60
gtcaagttgt ctgcggaagg acccactaca atgaccctcg tgtgcgggaa agatggagtc   120
aaagttcctc aagacaacaa tcagtactgt tccgggacga cgctgactgg ttgcaacgag   180
aaatcgttca agatatttt  gccaaaatta actgagaacc cgtggcaggg taacgcttcg   240
agtgataagg gtgccacgct aacgatcaag aaggaagcat tccagccga gtcaaaaagc    300 gtcattattg gatgcacagg gggatcgcct gagaagcatc actgtaccgt gaaactggag   360
tttgccgggg ctgcagggtc agcaaaatcg gct                                393
```

<210> SEQ ID NO 26
<211> LENGTH: 116
<212> TYPE: PRT
<213> ORGANISM: Toxoplasma gondii

<400> SEQUENCE: 26

```
Ser Gly Gly Thr Gly Gln Gly Leu Gly Ile Gly Glu Ser Val Asp Leu
  1               5                  10                  15

Glu Met Met Gly Asn Thr Tyr Arg Val Glu Arg Pro Thr Gly Asn Pro
             20                  25                  30

Asp Leu Leu Lys Ile Ala Ile Lys Ala Ser Asp Gly Ser Tyr Ser Glu
         35                  40                  45

Val Gly Asn Val Asn Val Glu Glu Val Ile Asp Thr Met Lys Ser Met
     50                  55                  60

Gln Arg Asp Glu Asp Ile Phe Leu Arg Ala Leu Asn Lys Gly Glu Thr
 65                  70                  75                  80

Val Glu Glu Ala Ile Glu Asp Val Ala Gln Ala Glu Gly Leu Asn Ser
                 85                  90                  95

Glu Gln Thr Leu Gln Leu Glu Asp Ala Val Ser Ala Val Ala Ser Val
            100                 105                 110

Val Gln Asp Glu
        115
```

<210> SEQ ID NO 27
<211> LENGTH: 55
<212> TYPE: PRT
<213> ORGANISM: Toxoplasma gondii

<400> SEQUENCE: 27

```
Tyr Ser Ser Pro Arg Ile Val Val Leu Ile Arg Tyr Cys Phe Phe Ser
  1               5                  10                  15

Thr Tyr Arg Leu Thr Met Phe Ala Val Lys His Cys Leu Leu Val Val
             20                  25                  30

Ala Val Gly Ala Leu Val Asn Val Ser Val Arg Ala Ala Glu Phe Ser
         35                  40                  45

Gly Val Val Asn Gln Gly Pro
     50                  55
```

<210> SEQ ID NO 28
<211> LENGTH: 99
<212> TYPE: PRT
<213> ORGANISM: Toxoplasma gondii

<400> SEQUENCE: 28

```
Ala Ala Leu Gly Gly Leu Ala Ala Asp Gln Pro Glu Asn His Gln Ala
  1               5                  10                  15

Leu Ala Glu Pro Val Thr Gly Val Gly Glu Ala Gly Val Ser Pro Val
```

```
                    20                  25                  30

Asn Glu Ala Gly Glu Ser Tyr Ser Ser Ala Thr Ser Gly Val Gln Glu
         35                  40                  45

Ala Thr Ala Pro Gly Ala Val Leu Leu Asp Ala Ile Asp Ala Glu Ser
 50                  55                  60

Asp Lys Val Asp Asn Gln Ala Glu Gly Gly Arg Met Lys Lys Val
 65                  70                  75                  80

Glu Glu Glu Leu Ser Leu Leu Arg Arg Glu Leu Tyr Asp Arg Thr Asp
                 85                  90                  95

Arg Pro Gly

<210> SEQ ID NO 29
<211> LENGTH: 78
<212> TYPE: PRT
<213> ORGANISM: Toxoplasma gondii

<400> SEQUENCE: 29

Phe Ala Thr Ala Ala Thr Ala Ser Asp Asp Glu Leu Met Ser Arg Ile
 1               5                  10                  15

Arg Asn Ser Asp Phe Phe Asp Gly Gln Ala Pro Val Asp Ser Leu Arg
                 20                  25                  30

Pro Thr Asn Ala Gly Val Asp Ser Lys Gly Thr Asp Asp His Leu Thr
         35                  40                  45

Thr Ser Met Asp Lys Ala Ser Val Glu Ser Gln Leu Pro Arg Arg Glu
 50                  55                  60

Pro Leu Glu Thr Glu Pro Asp Glu Gln Glu Glu Val His Phe
 65                  70                  75

<210> SEQ ID NO 30
<211> LENGTH: 35
<212> TYPE: PRT
<213> ORGANISM: Toxoplasma gondii

<400> SEQUENCE: 30

Glu Asn Pro Val Arg Pro Pro Pro Gly Phe His Pro Ser Val Ile
 1               5                  10                  15

Pro Asn Pro Pro Tyr Pro Leu Gly Thr Pro Ala Gly Met Pro Gln Pro
                 20                  25                  30

Glu Val Pro
         35

<210> SEQ ID NO 31
<211> LENGTH: 73
<212> TYPE: PRT
<213> ORGANISM: Toxoplasma gondii

<400> SEQUENCE: 31

Arg Arg Thr Gly Cys His Ala Phe Arg Glu Asn Cys Ser Pro Gly Arg
 1               5                  10                  15

Cys Ile Asp Asp Ala Ser His Glu Asn Gly Tyr Thr Cys Glu Cys Pro
                 20                  25                  30

Thr Gly Tyr Ser Arg Glu Val Thr Ser Lys Ala Glu Glu Ser Cys Val
         35                  40                  45

Glu Gly Val Glu Val Thr Leu Ala Glu Lys Cys Glu Lys Glu Phe Gly
 50                  55                  60

Ile Ser Ala Ser Ser Cys Lys Cys Asp
 65                  70
```

<210> SEQ ID NO 32
<211> LENGTH: 90
<212> TYPE: PRT
<213> ORGANISM: Toxoplasma gondii

<400> SEQUENCE: 32

```
Ala Pro Thr Gln Ser Glu Met Lys Glu Phe Gln Glu Ile Lys Glu
 1               5                  10                  15

Gly Val Glu Glu Thr Lys His Glu Asp Asp Pro Glu Met Thr Arg Leu
             20                  25                  30

Met Val Thr Glu Lys Gln Glu Ser Lys Asn Phe Ser Lys Met Ala Lys
         35                  40                  45

Ser Gln Ser Phe Ser Thr Arg Ile Glu Glu Leu Gly Gly Ser Ile Ser
     50                  55                  60

Phe Leu Thr Glu Thr Gly Val Thr Met Ile Glu Leu Pro Lys Thr Val
 65                  70                  75                  80

Ser Glu His Asp Met Asp Gln Leu Leu His
                 85                  90
```

<210> SEQ ID NO 33
<211> LENGTH: 152
<212> TYPE: PRT
<213> ORGANISM: Toxoplasma gondii

<400> SEQUENCE: 33

```
Val Met Ala Ser Asp Pro Pro Leu Val Ala Asn Gln Val Val Thr Cys
 1               5                  10                  15

Pro Asp Lys Lys Ser Thr Ala Ala Val Ile Leu Thr Pro Thr Glu Asn
             20                  25                  30

His Phe Thr Leu Lys Cys Pro Lys Thr Ala Leu Thr Glu Pro Pro Thr
         35                  40                  45

Leu Ala Tyr Ser Pro Asn Arg Gln Ile Cys Pro Ala Gly Thr Thr Ser
     50                  55                  60

Ser Cys Thr Ser Lys Ala Val Thr Leu Ser Ser Leu Ile Pro Glu Ala
 65                  70                  75                  80

Glu Asp Ser Trp Trp Thr Gly Asp Ser Ala Ser Leu Asp Thr Ala Gly
                 85                  90                  95

Ile Lys Leu Thr Val Pro Ile Glu Lys Phe Pro Val Thr Thr Gln Thr
            100                 105                 110

Phe Val Val Gly Cys Ile Lys Gly Asp Asp Ala Gln Ser Cys Met Val
        115                 120                 125

Thr Val Thr Val Gln Ala Arg Ala Ser Ser Val Val Asn Asn Val Ala
    130                 135                 140

Arg Cys Ser Tyr Gly Ala Asp Ser
145                 150
```

<210> SEQ ID NO 34
<211> LENGTH: 131
<212> TYPE: PRT
<213> ORGANISM: Toxoplasma gondii

<400> SEQUENCE: 34

```
Pro Ser Val Val Asn Asn Val Ala Arg Cys Ser Tyr Gly Ala Asp Ser
 1               5                  10                  15

Thr Leu Gly Pro Val Lys Leu Ser Ala Glu Gly Pro Thr Thr Met Thr
             20                  25                  30

Leu Val Cys Gly Lys Asp Gly Val Lys Val Pro Gln Asp Asn Asn Gln
```

```
                35                  40                  45
Tyr Cys Ser Gly Thr Thr Leu Thr Gly Cys Asn Glu Lys Ser Phe Lys
        50                  55                  60

Asp Ile Leu Pro Lys Leu Thr Glu Asn Pro Trp Gln Gly Asn Ala Ser
 65                  70                  75                  80

Ser Asp Lys Gly Ala Thr Leu Thr Ile Lys Lys Glu Ala Phe Pro Ala
                85                  90                  95

Glu Ser Lys Ser Val Ile Ile Gly Cys Thr Gly Ser Pro Glu Lys
            100                 105                 110

His His Cys Thr Val Lys Leu Glu Phe Ala Gly Ala Ala Gly Ser Ala
        115                 120                 125

Lys Ser Ala
    130

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
gatccttact agttttagta gcggccgcgg g                              31

<210> SEQ ID NO 36
<211> LENGTH: 31
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
aattcccgcg gccgctacta aaactagtaa g                              31

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
gggcactcga ccggaattat cg                                        22

<210> SEQ ID NO 38
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
gggtaaaggt ttctttgctc g                                         21

<210> SEQ ID NO 39
<211> LENGTH: 18
<212> TYPE: DNA
<213> ORGANISM: Artificial Sequence
<220> FEATURE:
<223> OTHER INFORMATION: Description of Artificial Sequence: Synthetic
```

-continued oligonucleotide

<400> SEQUENCE: 39
atggcggctg cacactcg                                                 18

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gaacatattc cctgtcacca atg                                           23

<210> SEQ ID NO 41
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 41
atgacgaaaa ataaaattct tctc                                          24

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 42
cattgatatc aacacaaagg cc                                            22

<210> SEQ ID NO 43
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 43
atggtgatga tgggcagcat g                                             21

<210> SEQ ID NO 44
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
cggcggccgc gctagagg                                                 18

<210> SEQ ID NO 45
<211> LENGTH: 34
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
cgttggatcc ttggattgag ccaaagggtg ccag                                      34

<210> SEQ ID NO 46
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 46
cccagaattc tcaagctgcc tgttccgcta agatctg                                   37

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atgacgggta ccgttagcag                                                      20

<210> SEQ ID NO 48
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
acccagcgcc gctaaactc                                                       19

<210> SEQ ID NO 49
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
atggtggtta tcaaggacat cg                                                   22

<210> SEQ ID NO 50
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ttttgggtgt cgaaagctct c                                                    21

<210> SEQ ID NO 51
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

45

-continued

```
<400> SEQUENCE: 51
atggcgccgt cagcatcg                                                   18

<210> SEQ ID NO 52
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 52
cttcacgctg atttgttgct ttg                                             23

<210> SEQ ID NO 53
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 53
atggacgaag cgagcagaag g                                               21

<210> SEQ ID NO 54
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 54
acgcgtgatc gaaggaaccg                                                 20

<210> SEQ ID NO 55
<211> LENGTH: 297
<212> TYPE: DNA
<213> ORGANISM: Toxoplasma gondii

<400> SEQUENCE: 55
ggattgagcc aaagggtgcc agagctacca gaagtggagc cctttgatga agtaggcacg     60
ggagctcgac ggtccgggtc cattgcgacc cttcttccac aagacgctgt tttatatgag    120
aactcagagg acgttgccgt tccgagtgat tcagcatcga ccccgtcata ctttcatgtg    180
gaatctccaa gtgctagtgt ggaagccgcg actggcgctg tgggagaggt ggtgccggac    240
tgtgaagaac aacaggaaca gggtgacacg acgttatccg atcacgattt ccattca       297

<210> SEQ ID NO 56
<211> LENGTH: 265
<212> TYPE: DNA
<213> ORGANISM: Toxoplasma gondii

<400> SEQUENCE: 56
tcttcagaaa gatgacgtaa ccatagaagt cgacaacgga gccatcgtta tcaaaggaga     60
gaagacctcg aaagaagcgg agaaagtgga cgatggcaaa acaaagaaca ttttgactga    120
gcgagtgtcc ggttattttg cgcgccggtt ccagctcccg agtaattaca agcccgacgg    180
aatcagtgcg gcaatggaca acggcgttct acgtgtcacg atcaaggtcg aggattcagg    240
gggcgcaaag caacaaatca gcgtg                                          265
```

```
<210> SEQ ID NO 57
<211> LENGTH: 98
<212> TYPE: PRT
<213> ORGANISM: Toxoplasma gondii

<400> SEQUENCE: 57

Gly Leu Ser Gln Arg Val Pro Glu Leu Pro Glu Val Glu Pro Phe Asp
  1               5                  10                  15

Glu Val Gly Thr Gly Ala Arg Arg Ser Gly Ser Ile Ala Thr Leu Leu
             20                  25                  30

Pro Gln Asp Ala Val Leu Tyr Glu Asn Ser Glu Asp Val Ala Val Pro
         35                  40                  45

Ser Asp Ser Ala Ser Thr Pro Ser Tyr Phe His Val Glu Ser Pro Ser
 50                  55                  60

Ala Ser Val Glu Ala Ala Thr Gly Ala Val Gly Val Val Pro Asp
 65                  70                  75                  80

Cys Glu Glu Gln Gln Glu Gln Gly Asp Thr Thr Leu Ser Asp His Asp
                 85                  90                  95

Phe His

<210> SEQ ID NO 58
<211> LENGTH: 135
<212> TYPE: PRT
<213> ORGANISM: Toxoplasma gondii

<400> SEQUENCE: 58

Leu Asn Pro Ile Asp Asp Met Leu Phe Glu Thr Ala Leu Thr Ala Asn
  1               5                  10                  15

Glu Met Met Glu Asp Ile Thr Trp Arg Pro Arg Val Asp Val Glu Phe
             20                  25                  30

Asp Ser Lys Lys Lys Glu Met Ile Ile Leu Ala Asp Leu Pro Gly Leu
         35                  40                  45

Gln Lys Asp Asp Val Thr Ile Glu Val Asp Asn Gly Ala Ile Val Ile
 50                  55                  60

Lys Gly Glu Lys Thr Ser Lys Glu Ala Glu Lys Val Asp Asp Gly Lys
 65                  70                  75                  80

Thr Lys Asn Ile Leu Thr Glu Arg Val Ser Gly Tyr Phe Ala Arg Arg
                 85                  90                  95

Phe Gln Leu Pro Ser Asn Tyr Lys Pro Asp Gly Ile Ser Ala Ala Met
            100                 105                 110

Asp Asn Gly Val Leu Arg Val Thr Ile Lys Val Glu Asp Ser Gly Gly
        115                 120                 125

Ala Lys Gln Gln Ile Ser Val
    130                 135

<210> SEQ ID NO 59
<211> LENGTH: 237
<212> TYPE: DNA
<213> ORGANISM: Toxoplasma gondii

<400> SEQUENCE: 59
ccccaggatg ccatttgctc ggattggtcc gcatggagcc cctgcagtgt atcctgcggt      60
gacggaagcc aaatcaggac gcgaactgag gtttctgctc cgcaacctgg aacaccaaca    120
tgtccggact gccctgcgcc catgggaagg acttgcgtgg aacaaggcgg acttgaagaa    180
atccgtgaat gcagtgcggg ggtatgtgct gttgacgctg gatgtggcgt ctgggtt       237
```

<210> SEQ ID NO 60
<211> LENGTH: 432
<212> TYPE: DNA
<213> ORGANISM: Toxoplasma gondii

<400> SEQUENCE: 60

| | | | | | |
|---|---|---|---|---|---:|
| ccgtgtccaa | ttaatgcaac | ttgcggtcag | tttgaagaat | ggagtacatg | ctcggtctca | 60 |
| tgtggtggtg | gactgaaaac | gaggtcgagg | aacccttgga | atgaagacca | acaacatgga | 120 |
| ggactatcct | gcgagcagca | gcatcctggt | gggcggacgg | aaacggtaac | ttgcaatcct | 180 |
| caagcgtgtc | ctgtggatga | acgaccgggg | gagtgggcag | agtgggggga | atgtagtgtc | 240 |
| acgtgcggcg | acggagtgcg | agagcgcagg | cgcgggaaaa | gtctagttga | ggctaaattc | 300 |
| ggcggacgca | ccattgatca | gcagaatgag | gctcttccgg | aagacttaaa | aatcaaaaac | 360 |
| gtcgagtatg | agccatgttc | gtatcctgct | tgtggagctt | cctgcacgta | cgtctggagt | 420 |
| gactggaaca | ag | | | | | 432 |

<210> SEQ ID NO 61
<211> LENGTH: 678
<212> TYPE: DNA
<213> ORGANISM: Toxoplasma gondii

<400> SEQUENCE: 61

| | | | | | |
|---|---|---|---|---|---:|
| aacgaaccgg | tggccctagc | tcagctcagc | acattcctcg | agctcgtcga | ggtgccatgt | 60 |
| aactctgttc | atgttcaggg | ggtgatgacc | ccgaatcaaa | tggtcaaagt | gactggtgca | 120 |
| ggatgggata | atggcgttct | cgagttctat | gtcacgaggc | caacgaagac | aggcggggac | 180 |
| acaagccgaa | gccatcttgc | gtcgatcatg | tgttattcca | aggacattga | cggcgtgccg | 240 |
| tcagacaaag | cgggaaagtg | ctttctgaag | aacttttctg | gtgaagactc | gtcggaaata | 300 |
| gacgaaaaag | aagtatctct | acccatcaag | agccacaacg | atgcgttcat | gttcgtttgt | 360 |
| tcttcaaatg | atggatccgc | actccagtgt | gatgttttcg | cccttgataa | caccaactct | 420 |
| agcgacgggt | ggaaagtgaa | taccgtggat | cttggcgtca | gcgttagtcc | ggatttggca | 480 |
| ttcggactca | ctgcagatgg | ggtcaaggtg | aagaagttgt | acgcaagcag | cggcctgaca | 540 |
| gcgatcaacg | acgacccttc | cttggggtgc | aaggctcctc | cccattctcc | gccggccgga | 600 |
| gaggaaccga | gtttgccgtc | gcctgaaaac | agcgggtctg | caacaccagc | ggaagaaagt | 660 |
| ccgtctgagt | ctgaatct | | | | | 678 |

<210> SEQ ID NO 62
<211> LENGTH: 582
<212> TYPE: DNA
<213> ORGANISM: Toxoplasma gondii

<400> SEQUENCE: 62

| | | | | | |
|---|---|---|---|---|---:|
| cttcgcgggt | acaggttcgg | tgtttggaag | aaaggccgtt | gcctcgacta | cactgaattg | 60 |
| accgacactg | tgatagaacg | tgttgagtca | aaggcacagt | gctgggtgaa | aacctttgaa | 120 |
| aacgacgggg | tcgcgagtga | ccaaccccat | acgtatccac | tgacgtcgca | agcatcatgg | 180 |
| aacgattggt | ggcctctcca | ccagagtgac | caacctcact | caggtggcgt | tgggcgtaat | 240 |
| tacggttct | actacgtgga | cacgactgga | gagggcaagt | gtgcactctc | tgaccaggta | 300 |
| cccgactgcc | tggtgtcgga | ttctgccgcc | gtgtcgtata | cagcagcggg | gagtttgtct | 360 |
| gaagagacgc | cgaatttcat | aattccgtca | aatccctctg | ttactccgcc | aacgcccgag | 420 |
| acggcacttc | agtgcacggc | cgacaagttc | cccgactctt | tcggtgcctg | cgacgttcaa | 480 |

-continued

```
gcctgtaaaa gacagaagac gtcctgcgtt ggcggacaga ttcaaagtac tagcgtcgac    540
tgcaccgcgg acgaacaaaa tgaatgtggc tctaacactg cg                       582
```

<210> SEQ ID NO 63
<211> LENGTH: 507
<212> TYPE: DNA
<213> ORGANISM: Toxoplasma gondii

<400> SEQUENCE: 63

```
agtgccaacg taacaagttc ggagcctgca aaacttgatc tctcttgtgc gcactctgac     60
aataagggat caagggctcc cacaataggc gagccagtgc cagatgtgtc cctggaacaa    120
tgtgctgcgc aatgcaaggc tgttgatggc tgcacacatt tcacttataa tgacgattcg    180
aagatgtgcc atgtgaagga gggaaaaccc gatttatacg atctcacagg aggcaaaaca    240
gcaccgcgca gttgcgatag atcatgcttc gaacaacacg tatcgtatga gggagctcct    300
gacgtgatga cagcgatggt cacgagccag tcagcggact gtcaggctgc gtgtgcggct    360
gacccgagct gcgagatctt cacttataac gaacacgacc agaaatgtac tttcaaagga    420
aggggttttt ctgcgtttaa ggaacgaggg gtgttgggtg tgacttccgg gccgaaacag    480
ttctgcgatg aaggcggtaa attaact                                        507
```

<210> SEQ ID NO 64
<211> LENGTH: 79
<212> TYPE: PRT
<213> ORGANISM: Toxoplasma gondii

<400> SEQUENCE: 64

```
Pro Gln Asp Ala Ile Cys Ser Asp Trp Ser Ala Trp Ser Pro Cys Ser
  1               5                  10                  15

Val Ser Cys Gly Asp Gly Ser Gln Ile Arg Thr Arg Thr Glu Val Ser
             20                  25                  30

Ala Pro Gln Pro Gly Thr Pro Thr Cys Pro Asp Cys Pro Ala Pro Met
         35                  40                  45

Gly Arg Thr Cys Val Glu Gln Gly Gly Leu Glu Glu Ile Arg Glu Cys
     50                  55                  60

Ser Ala Gly Val Cys Ala Val Asp Ala Gly Cys Gly Val Trp Val
 65                  70                  75
```

<210> SEQ ID NO 65
<211> LENGTH: 144
<212> TYPE: PRT
<213> ORGANISM: Toxoplasma gondii

<400> SEQUENCE: 65

```
Pro Cys Pro Ile Asn Ala Thr Cys Gly Gln Phe Glu Glu Trp Ser Thr
  1               5                  10                  15

Cys Ser Val Ser Cys Gly Gly Gly Leu Lys Thr Arg Ser Arg Asn Pro
             20                  25                  30

Trp Asn Glu Asp Gln Gln His Gly Gly Leu Ser Cys Glu Gln Gln His
         35                  40                  45

Pro Gly Gly Arg Thr Glu Thr Val Thr Cys Asn Pro Gln Ala Cys Pro
     50                  55                  60

Val Asp Glu Arg Pro Gly Glu Trp Ala Glu Trp Gly Glu Cys Ser Val
 65                  70                  75                  80

Thr Cys Gly Asp Gly Val Arg Glu Arg Arg Gly Lys Ser Leu Val
             85                  90                  95
```

```
Glu Ala Lys Phe Gly Gly Arg Thr Ile Asp Gln Gln Asn Glu Ala Leu
                100                 105                 110

Pro Glu Asp Leu Lys Ile Lys Asn Val Glu Tyr Glu Pro Cys Ser Tyr
            115                 120                 125

Pro Ala Cys Gly Ala Ser Cys Thr Tyr Val Trp Ser Asp Trp Asn Lys
    130                 135                 140

<210> SEQ ID NO 66
<211> LENGTH: 226
<212> TYPE: PRT
<213> ORGANISM: Toxoplasma gondii

<400> SEQUENCE: 66

Asn Glu Pro Val Ala Leu Ala Gln Leu Ser Thr Phe Leu Glu Leu Val
  1               5                  10                  15

Glu Val Pro Cys Asn Ser Val His Val Gln Gly Val Met Thr Pro Asn
             20                  25                  30

Gln Met Val Lys Val Thr Gly Ala Gly Trp Asp Asn Gly Val Leu Glu
         35                  40                  45

Phe Tyr Val Thr Arg Pro Thr Lys Thr Gly Gly Asp Thr Ser Arg Ser
     50                  55                  60

His Leu Ala Ser Ile Met Cys Tyr Ser Lys Asp Ile Asp Gly Val Pro
 65                  70                  75                  80

Ser Asp Lys Ala Gly Lys Cys Phe Leu Lys Asn Phe Ser Gly Glu Asp
                 85                  90                  95

Ser Ser Glu Ile Asp Glu Lys Glu Val Ser Leu Pro Ile Lys Ser His
            100                 105                 110

Asn Asp Ala Phe Met Phe Val Cys Ser Ser Asn Asp Gly Ser Ala Leu
            115                 120                 125

Gln Cys Asp Val Phe Ala Leu Asp Asn Thr Asn Ser Ser Asp Gly Trp
    130                 135                 140

Lys Val Asn Thr Val Asp Leu Gly Val Ser Val Ser Pro Asp Leu Ala
145                 150                 155                 160

Phe Gly Leu Thr Ala Asp Gly Val Lys Val Lys Lys Leu Tyr Ala Ser
                165                 170                 175

Ser Gly Leu Thr Ala Ile Asn Asp Asp Pro Ser Leu Gly Cys Lys Ala
            180                 185                 190

Pro Pro His Ser Pro Pro Ala Gly Glu Glu Pro Ser Leu Pro Ser Pro
        195                 200                 205

Glu Asn Ser Gly Ser Ala Thr Pro Ala Glu Glu Ser Pro Ser Glu Ser
    210                 215                 220

Glu Ser
225

<210> SEQ ID NO 67
<211> LENGTH: 194
<212> TYPE: PRT
<213> ORGANISM: Toxoplasma gondii

<400> SEQUENCE: 67

Leu Arg Gly Tyr Arg Phe Gly Val Trp Lys Lys Gly Arg Cys Leu Asp
  1               5                  10                  15

Tyr Thr Glu Leu Thr Asp Thr Val Ile Glu Arg Val Glu Ser Lys Ala
             20                  25                  30

Gln Cys Trp Val Lys Thr Phe Glu Asn Asp Gly Val Ala Ser Asp Gln
         35                  40                  45
```

```
Pro His Thr Tyr Pro Leu Thr Ser Gln Ala Ser Trp Asn Asp Trp Trp
         50                  55                  60

Pro Leu His Gln Ser Asp Gln Pro His Ser Gly Gly Val Gly Arg Asn
 65                  70                  75                  80

Tyr Gly Phe Tyr Tyr Val Asp Thr Thr Gly Glu Gly Lys Cys Ala Leu
                 85                  90                  95

Ser Asp Gln Val Pro Asp Cys Leu Val Ser Asp Ser Ala Ala Val Ser
            100                 105                 110

Tyr Thr Ala Ala Gly Ser Leu Ser Glu Glu Thr Pro Asn Phe Ile Ile
            115                 120                 125

Pro Ser Asn Pro Ser Val Thr Pro Thr Pro Glu Thr Ala Leu Gln
        130                 135                 140

Cys Thr Ala Asp Lys Phe Pro Asp Ser Phe Gly Ala Cys Asp Val Gln
145                 150                 155                 160

Ala Cys Lys Arg Gln Lys Thr Ser Cys Val Gly Gly Gln Ile Gln Ser
                165                 170                 175

Thr Ser Val Asp Cys Thr Ala Asp Glu Gln Asn Glu Cys Gly Ser Asn
            180                 185                 190

Thr Ala

<210> SEQ ID NO 68
<211> LENGTH: 169
<212> TYPE: PRT
<213> ORGANISM: Toxoplasma gondii

<400> SEQUENCE: 68

Ser Ala Asn Val Thr Ser Ser Glu Pro Ala Lys Leu Asp Leu Ser Cys
 1               5                  10                  15

Ala His Ser Asp Asn Lys Gly Ser Arg Ala Pro Thr Ile Gly Glu Pro
            20                  25                  30

Val Pro Asp Val Ser Leu Glu Gln Cys Ala Ala Gln Cys Lys Ala Val
        35                  40                  45

Asp Gly Cys Thr His Phe Thr Tyr Asn Asp Asp Ser Lys Met Cys His
 50                  55                  60

Val Lys Glu Gly Lys Pro Asp Leu Tyr Asp Leu Thr Gly Gly Lys Thr
 65                  70                  75                  80

Ala Pro Arg Ser Cys Asp Arg Ser Cys Phe Glu Gln His Val Ser Tyr
                 85                  90                  95

Glu Gly Ala Pro Asp Val Met Thr Ala Met Val Thr Ser Gln Ser Ala
            100                 105                 110

Asp Cys Gln Ala Ala Cys Ala Ala Asp Pro Ser Cys Glu Ile Phe Thr
            115                 120                 125

Tyr Asn Glu His Asp Gln Lys Cys Thr Phe Leu Gly Arg Gly Phe Ser
130                 135                 140

Ala Phe Lys Glu Arg Gly Val Leu Gly Val Thr Ser Gly Pro Lys Gln
145                 150                 155                 160

Phe Cys Asp Glu Gly Gly Lys Leu Thr
                165

<210> SEQ ID NO 69
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
```

<400> SEQUENCE: 69
atgagactcc aaccgaggcc                                                    20

<210> SEQ ID NO 70
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 70
ctgcctgact ctttcttgga ctg                                                23

<210> SEQ ID NO 71
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 71
ggaaagttgg aaatccggcg gc                                                 22

<210> SEQ ID NO 72
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 72
cgcctcatcg tcactcggc                                                     19

<210> SEQ ID NO 73
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 73
atgagagcgt cgctcccgg                                                     19

<210> SEQ ID NO 74
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
gtgtctttcg cttcaagcac ctg                                                23

<210> SEQ ID NO 75
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide -continued

```
<400> SEQUENCE: 75
atggggctcg tgggcgtac                                          19

<210> SEQ ID NO 76
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
gatcaacgca gtgttagagc cac                                     23
```